US008637065B2

(12) United States Patent
Athanasiou et al.

(10) Patent No.: US 8,637,065 B2
(45) Date of Patent: Jan. 28, 2014

(54) DERMIS-DERIVED CELLS FOR TISSUE ENGINEERING APPLICATIONS

(75) Inventors: Kyriacos A. Athanasiou, Houston, TX (US); Ying Deng, Sioux Falls, SD (US); Jerry Hu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 856 days.

(21) Appl. No.: 12/246,320

(22) Filed: Oct. 6, 2008

(65) Prior Publication Data

US 2009/0155333 A1 Jun. 18, 2009

Related U.S. Application Data

(63) Continuation-in-part of application No. 11/571,790, filed on Aug. 23, 2010, which is a continuation of application No. PCT/US2005/024269, filed on Jul. 8, 2005, application No. 12/246,320, which is a continuation-in-part of application No. PCT/US2007/066089, filed on Apr. 5, 2007, and a continuation-in-part of application No. PCT/US2007/066085, filed on Apr. 5, 2007, and a continuation-in-part of application No. PCT/US2007/066092, filed on Apr. 5, 2007.

(60) Provisional application No. 60/586,862, filed on Jul. 9, 2004, provisional application No. 60/789,851, filed on Apr. 5, 2006, provisional application No. 60/789,853, filed on Apr. 5, 2006, provisional application No. 60/789,855, filed on Apr. 5, 2006.

(51) Int. Cl.
*A61F 2/08* (2006.01)
*C12N 5/077* (2010.01)

(52) U.S. Cl.
USPC ............ 424/423; 435/377; 435/397; 435/402

(58) Field of Classification Search
USPC .......................... 424/423; 435/377, 397, 402
See application file for complete search history.

(56) References Cited

U.S. PATENT DOCUMENTS

| | | | | |
|---|---|---|---|---|
| 5,842,477 | A * | 12/1998 | Naughton et al. | 128/898 |
| 5,882,929 | A * | 3/1999 | Fofonoff et al. | 435/395 |
| 6,027,744 | A * | 2/2000 | Vacanti et al. | 424/426 |
| 6,197,586 | B1 * | 3/2001 | Bhatnagar et al. | 435/395 |
| 2002/0132346 | A1 | 9/2002 | Cibelli | |
| 2002/0146401 | A1 | 10/2002 | Bell et al. | |
| 2003/0215426 | A1 * | 11/2003 | French et al. | 424/93.7 |
| 2004/0082063 | A1 | 4/2004 | Deshpande et al. | |

FOREIGN PATENT DOCUMENTS

| | | |
|---|---|---|
| WO | WO 9717038 | 5/1997 |
| WO | WO 0052145 | 9/2000 |
| WO | WO 0210347 | 2/2002 |
| WO | WO 0210348 | 2/2002 |
| WO | WO 03050250 | 6/2003 |
| WO | WO 2006/017176 A2 | 2/2006 |

OTHER PUBLICATIONS

Deng et al. Isolation and Chondroinduction of a Dermis-Isolated, Aggrecan-Sensitive Subpopulation With High Chondrogenic Potential. Arthritis & Rheumatism vol. 56, No. 1, Jan. 2007, pp. 168-176.*
Mainil-Varlet et al.: "Articular cartilage repair using a tissue-engineered cartilage-like implant: an animal study." Osteoarthritis and Cartilage, 2001, vol. 9, pp. S6-S15.
Hung et al.: "Anatomically shaped osteochondral constructs for articular cartilage repair." Journal of Biomechanics, 2003, vol. 36(12), pp. 1853-1864.
Aufderheide et al.: "Assessment of a Bovine Co-culture, Scaffold-Free Method for Growing Meniscus-Shaped Constructs." Tissue Engineering, 2007, vol. 13(9), pp. 2195-2205.
Hu et al.: "A Self-Assembling Processes in Articular Cartilage Tissue Engineering." Tissue Engineering, 2006, vol. 12(4), pp. 969-979.
Masuda et al.: "A novel two-step method for the formation of tissue-engineered cartilage by mature bovine chondrocytes: the alginate-recovered-chondorcyte (ARC) method/" Journal of Orthopaedic Research, 2003, vol. 21 (1), pp. 139-148.
Hoben et al.: "Self-Assembly of Fibrochondrocytes and Chondrocytes for Tissue Engineering of the Knee Meniscus." Tissue Engineering, 2007, vol. 13(5), 2007, pp. 939-946.
French et al.: "Chondrogenic Differentiation of Adult Dermal Fibroblasts." Annals of Biomedical Engineering, Jan. 2004, vol. 32(1), pp. 50-56.
Kisiday et al.: "Teach self assembly peptide hydrogel fosters chondrocyte extracellular matrix production and cell division for cartilage tissue repair." PNAS, Jul. 23, 2002; vol. 99(15), pp. 9996-10001.
Sweigart et al.: "Fibrochondrocytes and Their Use in Tissue Engineering of the Meniscus." Topics in Tissue Engineering 2003, Chapter 1.
Dessau et al.: "Extracellular Matrix Formation by Chondrocytes in Monolayer Culture." The Journal of Cell Biology, Jul. 1981, vol. 90, pp. 78-83.
Khoo, M.L.M. et al.: "Growth and Differentiation of Embryoid Bodies from Human Embryonic Stem Cells: Effect of Glucose and Basic Fibroblast Growth Factor." Biology of Reproduction, 2005, vol. 73, pp. 1147-1156.
Heng, B.C. et al.: "Directing Stem Cell Differentiation into the Chondrogenic Lineage in Vitro." Stem Cells, 2004, vol. 22, pp. 1152-1167.
Tacchetti C., et al.: "In vitro morphogenesis of chick embryo hypertrophic cartilage." The Journal of Cell Biology, vol. 105, No. 2, Aug. 1, 1987, pp. 999-1006, XP002485820.
Turnay J., et al.: "Changes in the expression of annexin A5 gene during in vitro chondrocyte differentiation: influence of cell attachment." Journal of Cellular Biochemistry, vol. 84, No. 1, 2002, pp. 132-142, XP002971303.

(Continued)

*Primary Examiner* — Taeyoon Kim
(74) *Attorney, Agent, or Firm* — Robert R. Riddle; Reed Smith LLP

(57) ABSTRACT

Methods for inducing differentiation of dermis-derived cells to serve as a source of chondrocytes and associated methods of use in forming tissue engineered constructs. One example of a method is a method for inducing differentiation of cells into chondrocytes comprising providing aggrecan sensitive isolated dermis cells and seeding the cells onto an aggrecan coated surface.

18 Claims, 28 Drawing Sheets
(27 of 28 Drawing Sheet(s) Filed in Color)

(56) References Cited

OTHER PUBLICATIONS

Sabbatini A., et al.: "Use of human chondrocyte cell cultures to identify and characterize reactive antibodies in rheumatoid arthritis sera." Clinical and Experimental Rheumatology, vol. 21, No. 5, Sep. 2003, pp. 587-592, XP008092656.

Lebaron R.G. and Athanasiou K.A.: "Ex vivo synthesis of articular cartilage." Biomaterials, vol. 21, No. 24, Dec. 2000, pp. 2575-2587, XP004217421.

Mauck R.L., et al.: "The role of cell seeding density and nutrient supply for articular cartilage tissue engineering with deformational loading." Osteoarthritis and Cartilage, vol. 11, No. 12, Dec. 2003, pp. 879-890, XP002485821.

Kokenyesi, et al.: "Archives of Biochemistry and Biophysics." vol. 383, Nov. 1, 2000, pp. 79-90.

European Search report dated Jul. 29, 2008 for PCT/US2005024269.

International Search report dated Feb. 26, 2008 for PCT/US2007/066089.

International Search report dated Aug. 13, 2008 for PCT/US07/66085.

International Search report dated Mar. 27, 2008 for PCT/US2007/066092.

* cited by examiner

FIGURE 2
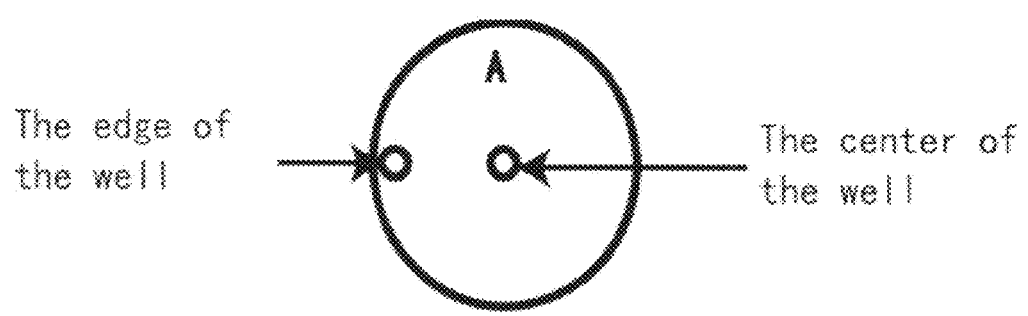
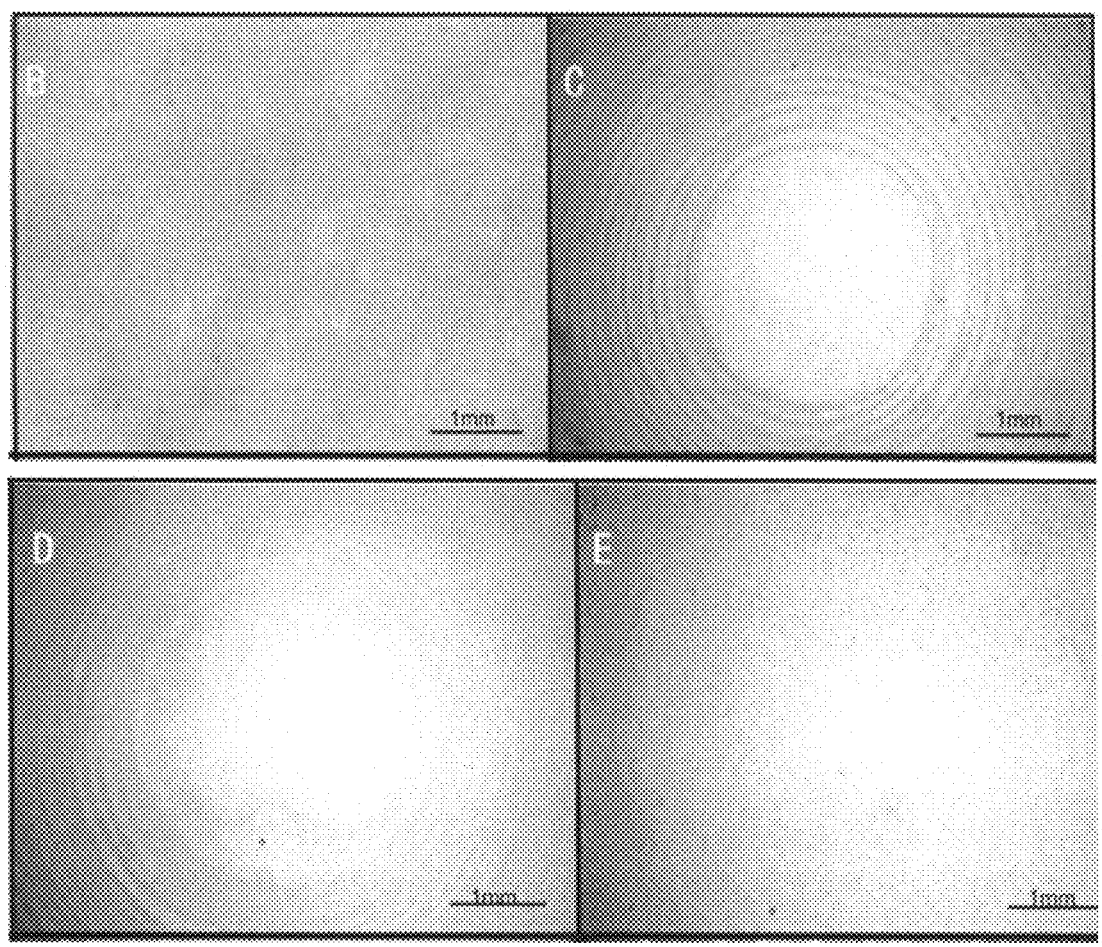

FIGURE 2 (Cont.)
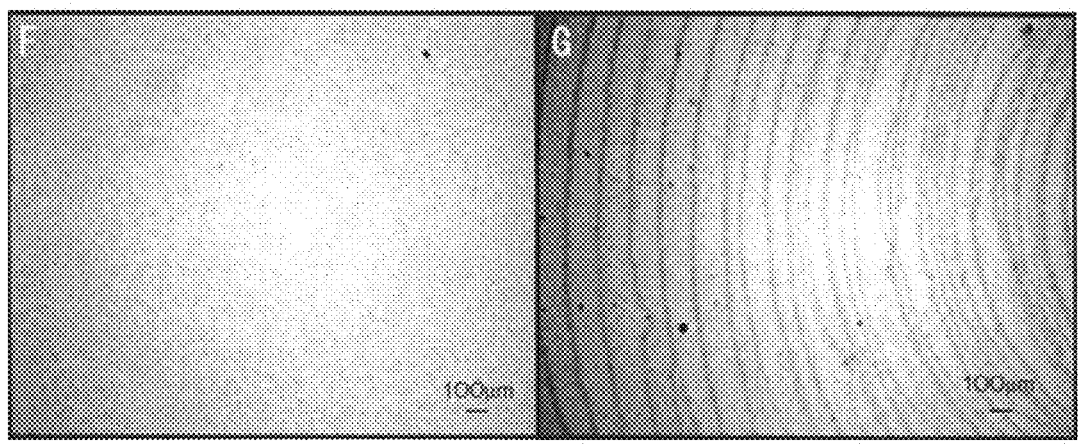
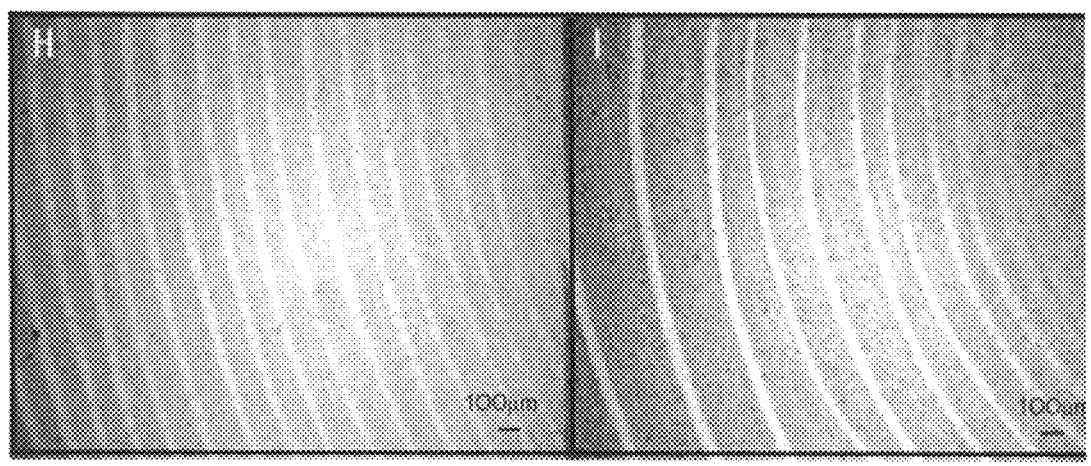

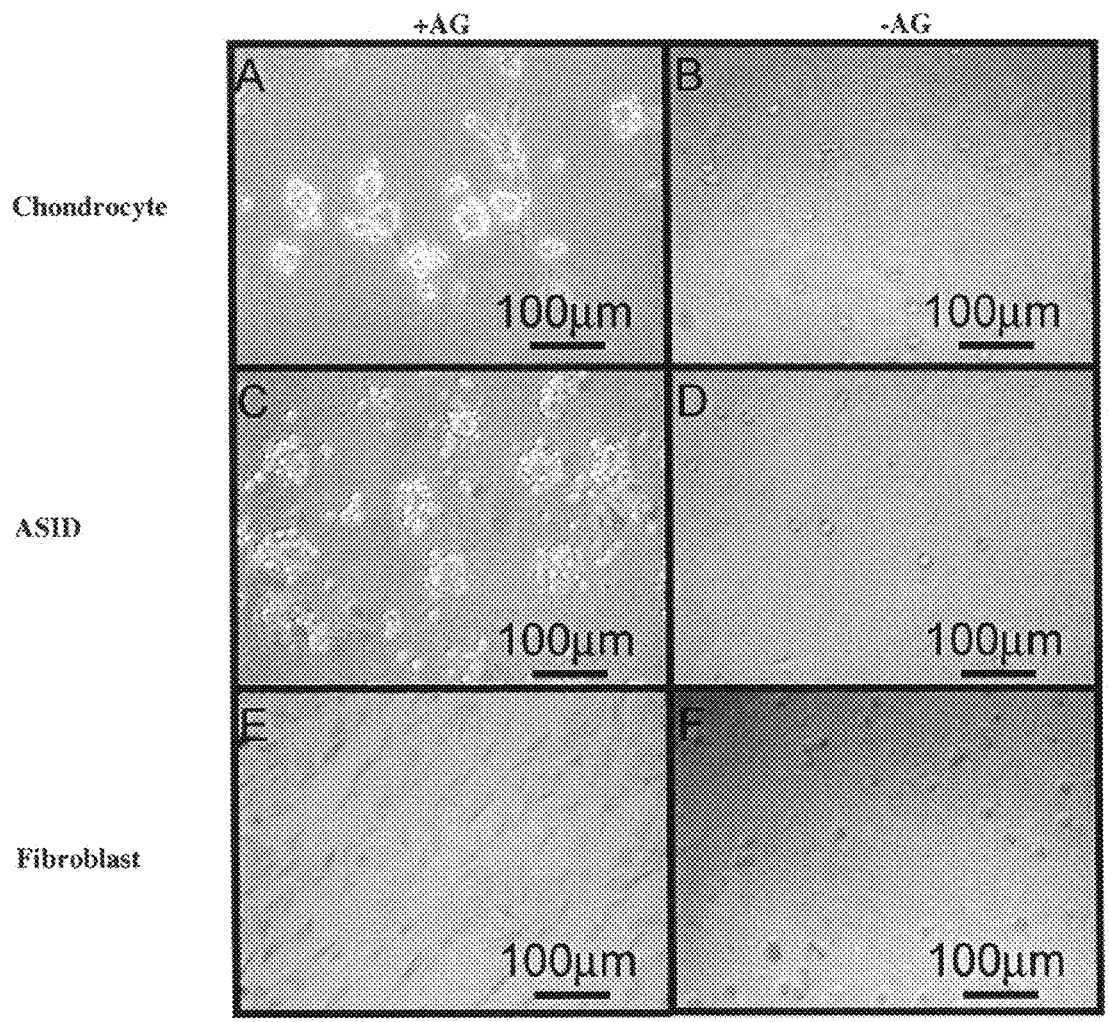

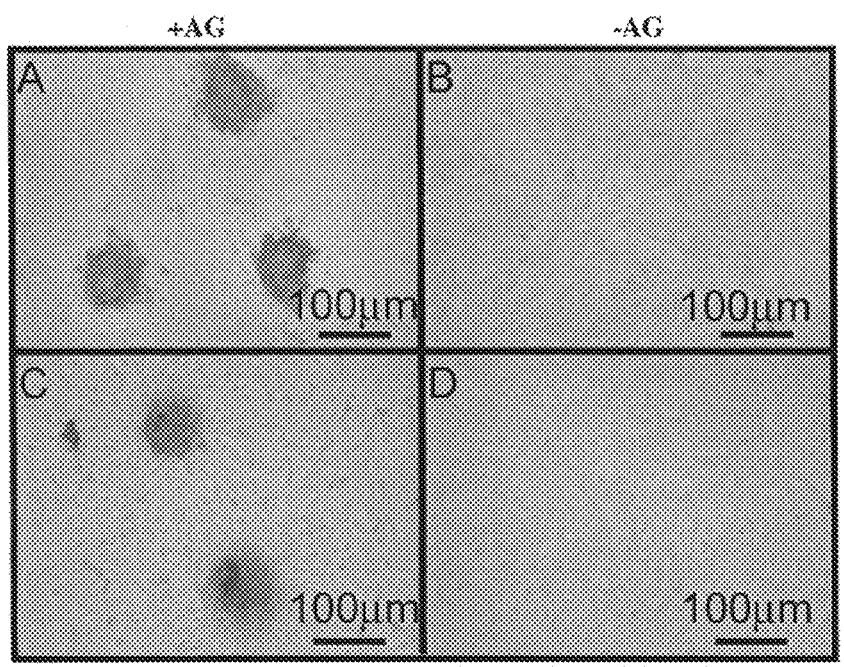

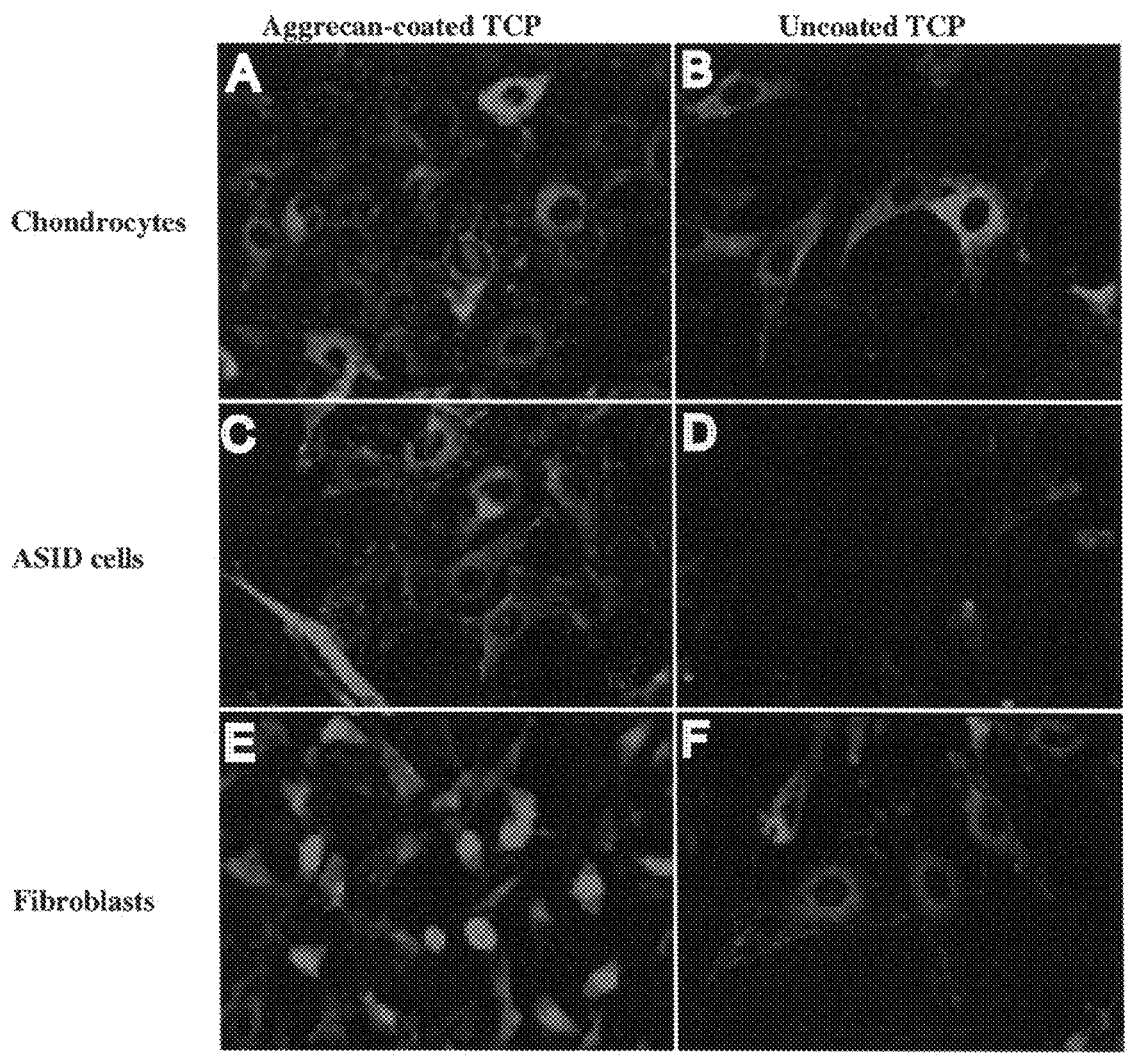

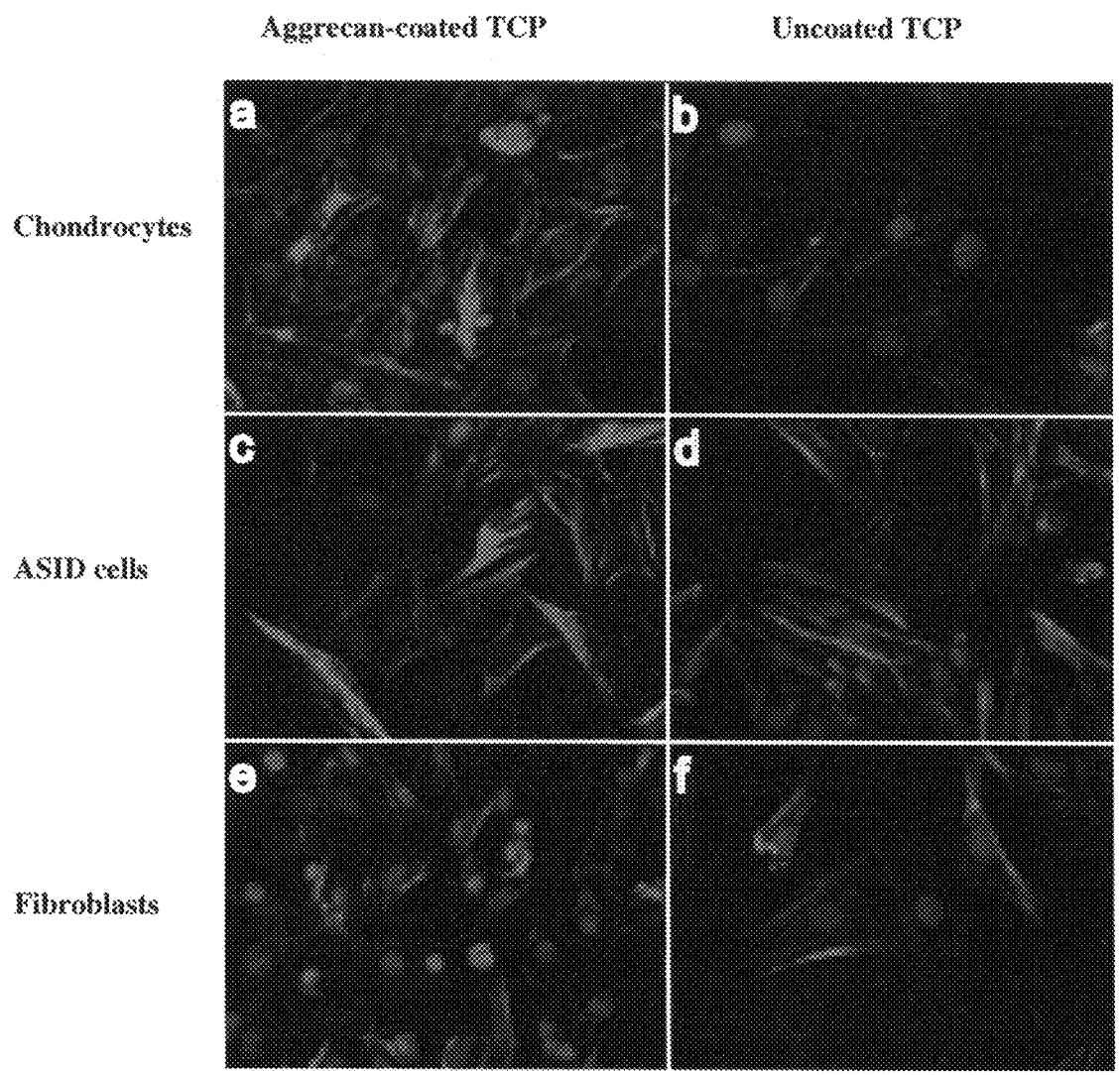

FIGURE 10
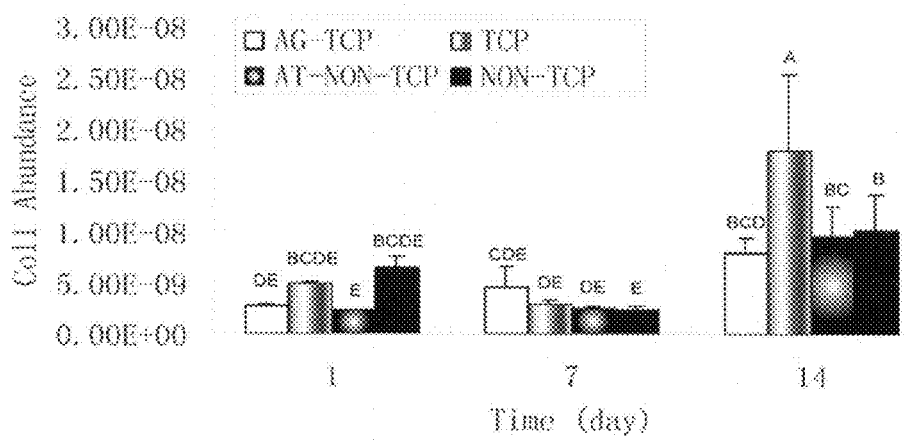
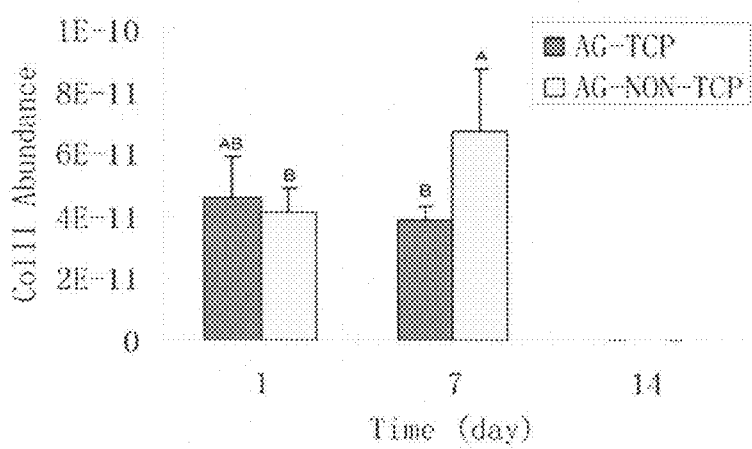
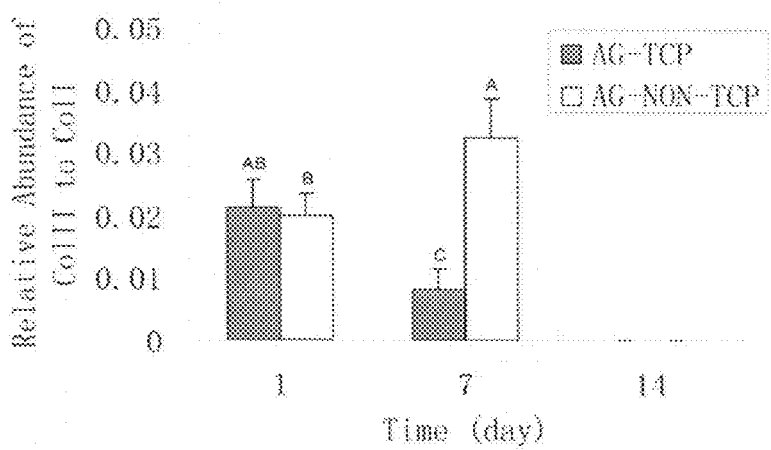

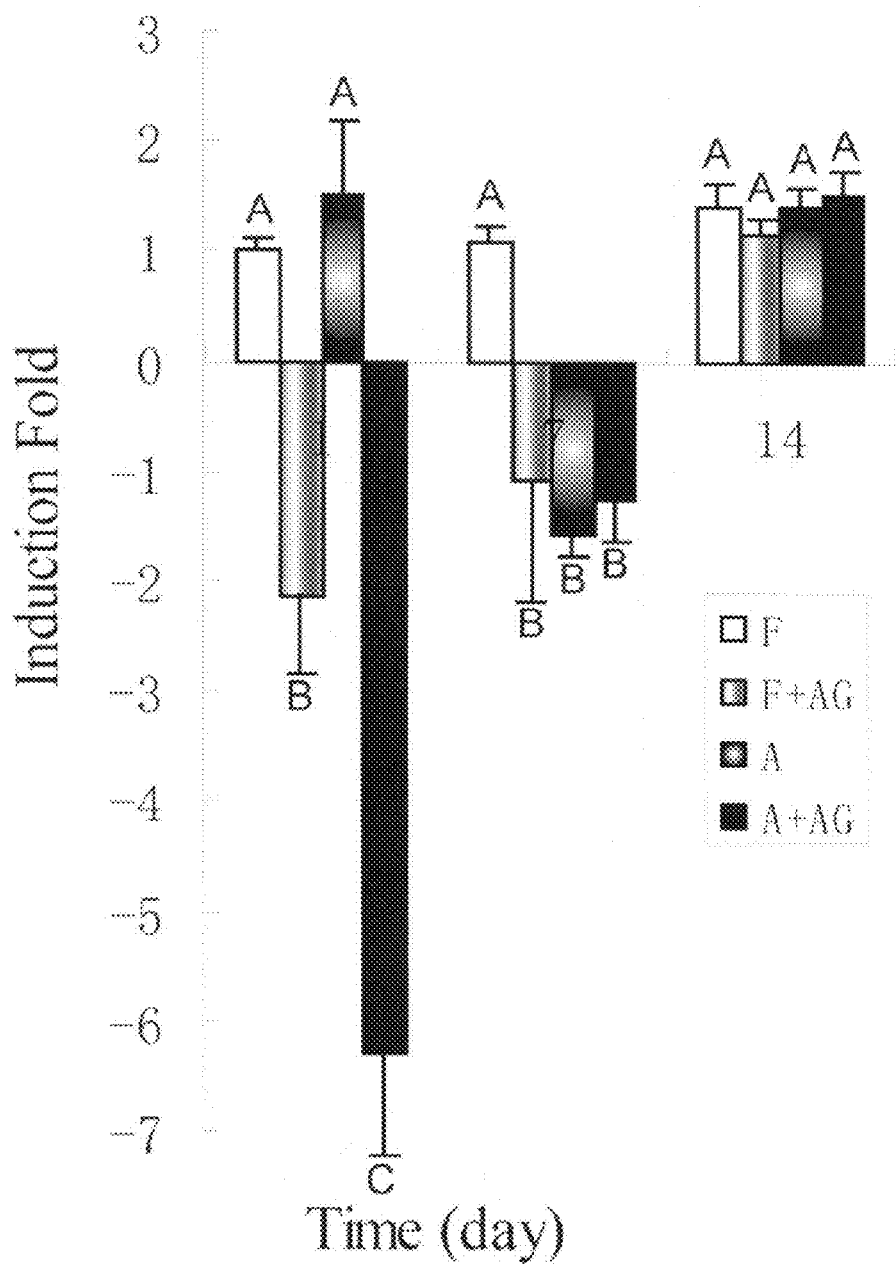

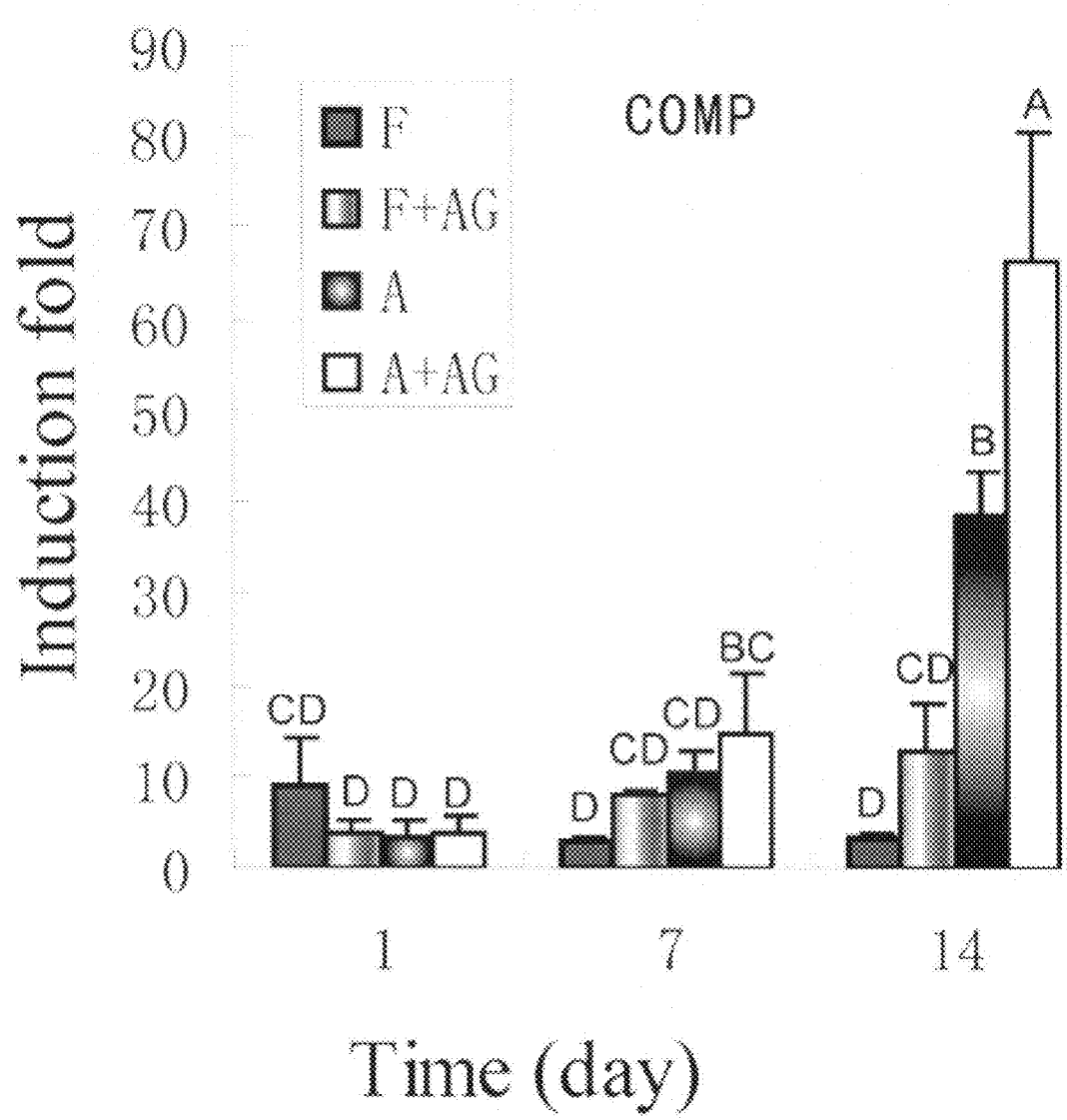

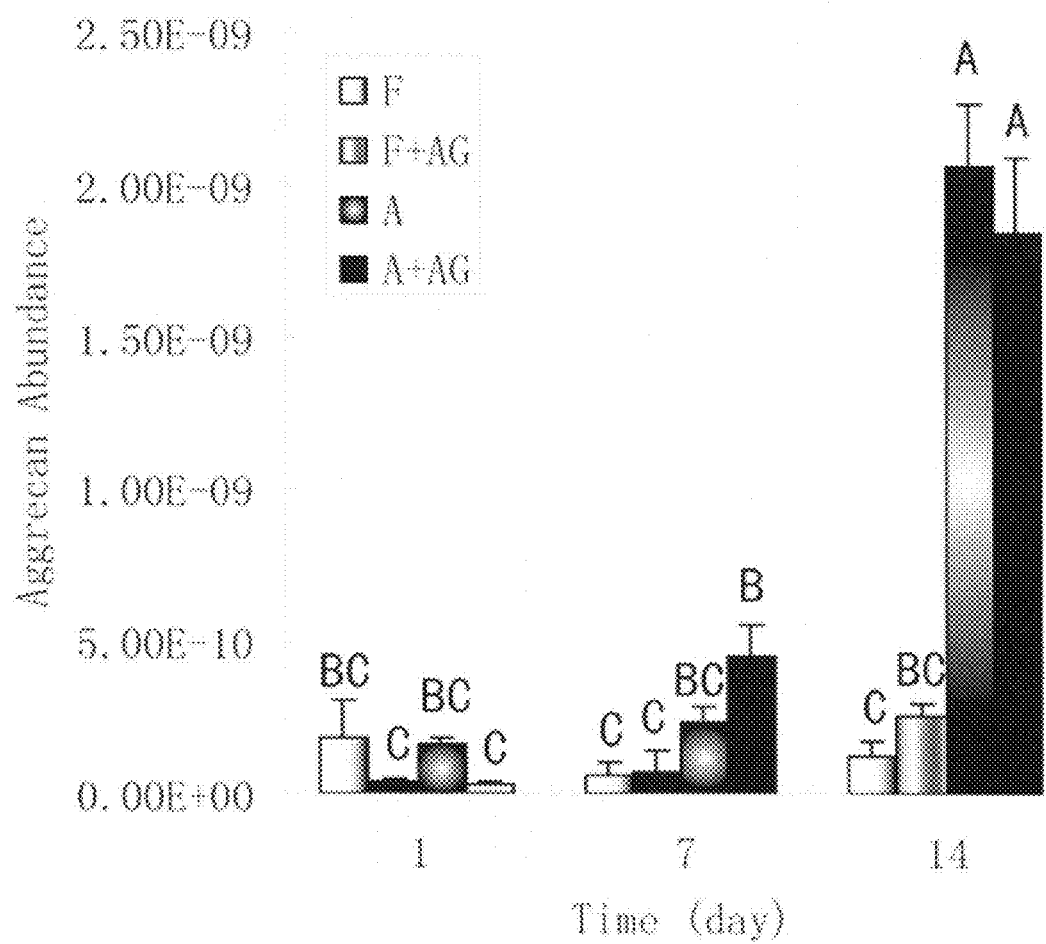

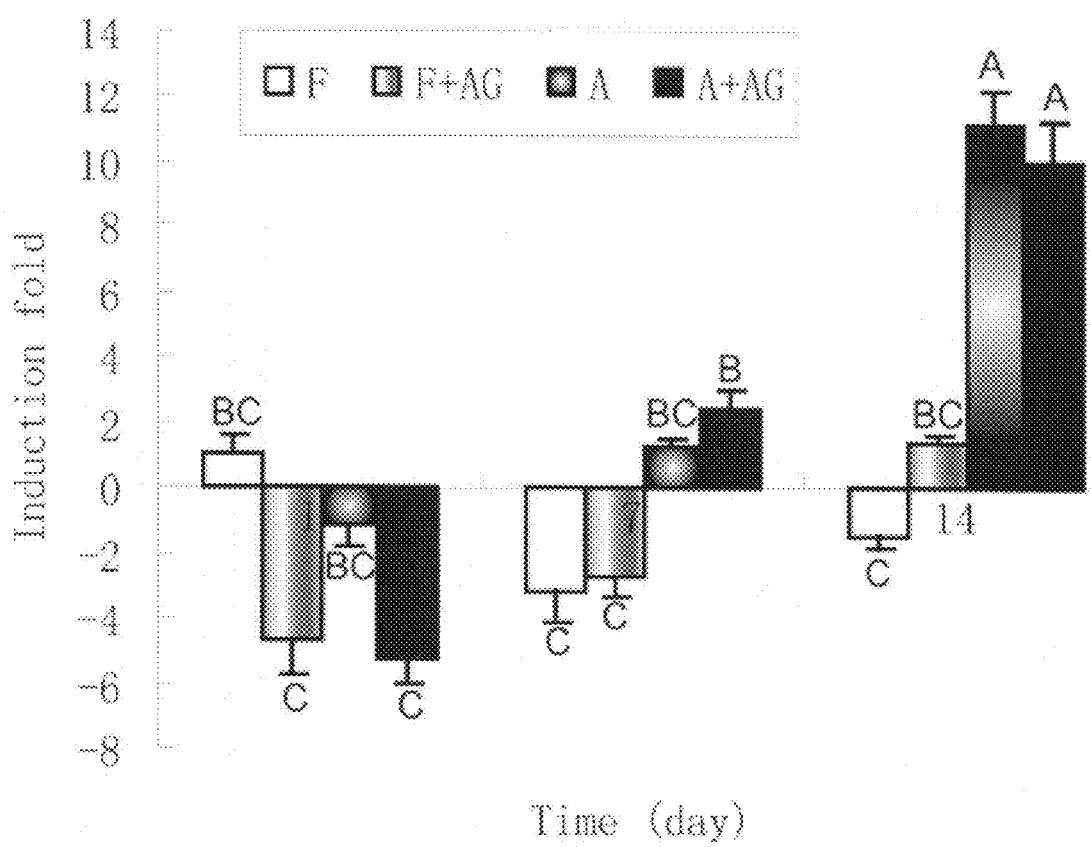

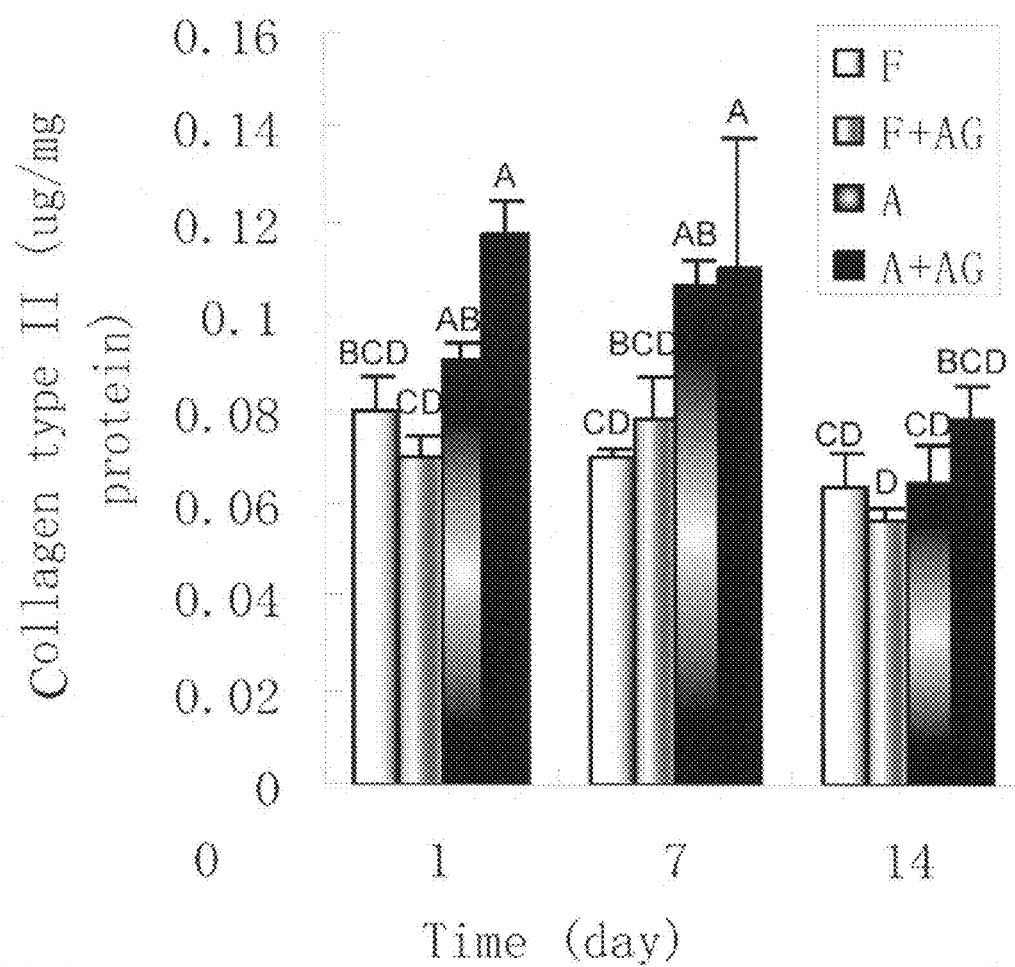

SEQUENCE LISTING

<160> NUMBER OF SEQ ID NOS: 12

<210> SEQ ID NO 1
<211> LENGTH: 20
<212> TYPE: DNA
<213> ORGANISM: Artificial, Natural, or Synthetic Sequence
<220> FEATURE:
<223> OTHER INFORMATION: GADPH Primer Forward Sequence

<400> SEQUENCE: 1
accctcaaga ttgtcagcaa                                            20

<210> SEQ ID NO 2
<211> LENGTH: 18
<212> TYPE: DNA
<213> ORGANISM: Artificial, Natural, or Synthetic Sequence
<220> FEATURE:

<223> OTHER INFORMATION: GADPH Primer Reverse Sequence

<400> SEQUENCE: 2
acgatgccaa agtggtca                                                         18

<210> SEQ ID NO 3
<211> LENGTH: 22
<212> TYPE: DNA
<213> ORGANISM: Artificial, Natural, or Synthetic Sequence
<220> FEATURE:
<223> OTHER INFORMATION: GADPH Primer Probe Sequence

<400> SEQUENCE: 3
cctcctgcac caccaactgc tt                                                    22

<210> SEQ ID NO 4
<211> LENGTH: 20
<212> TYPE: DNA
<213> ORGANISM: Artificial, Natural, or Synthetic Sequence
<220> FEATURE:
<223> OTHER INFORMATION: Type I collagen Primer Forward Sequence

<400> SEQUENCE: 4
cattaggggt cacaatggtc                                                       20

<210> SEQ ID NO 5
<211> LENGTH: 20
<212> TYPE: DNA
<213> ORGANISM: Artificial, Natural, or Synthetic Sequence
<220> FEATURE:
<223> OTHER INFORMATION: Type I collagen Primer Reverse Sequence

<400> SEQUENCE: 5
tggagttcca ttttcaccag                                                       20

<210> SEQ ID NO 6
<211> LENGTH: 24
<212> TYPE: DNA
<213> ORGANISM: Artificial, Natural, or Synthetic Sequence
<220> FEATURE:
<223> OTHER INFORMATION: Type I collagen Primer Probe Sequence

<400> SEQUENCE: 6
atggatttga agggacagcc tggt                                                  24

<210> SEQ ID NO 7
<211> LENGTH: 18
<212> TYPE: DNA
<213> ORGANISM: Artificial, Natural, or Synthetic Sequence
<220> FEATURE:
<223> OTHER INFORMATION: Type II collagen Primer Forward Sequence

<400> SEQUENCE: 7
aacggtggct tccacttc                                                         18

<210> SEQ ID NO 8
<211> LENGTH: 18
<212> TYPE: DNA
<213> ORGANISM: Artificial, Natural, or Synthetic Sequence
<220> FEATURE:
<223> OTHER INFORMATION: Type II collagen Primer Reverse Sequence

<400> SEQUENCE: 8
gcaggaaggt catctgga                                                         18

<210> SEQ ID NO 9

-continued

```
<211> LENGTH: 23
<212> TYPE: DNA
<213> ORGANISM: Artificial, Natural, or Synthetic Sequence
<220> FEATURE:
<223> OTHER INFORMATION: Type II collagen Primer Probe Sequence

<400> SEQUENCE: 9
atgacaacct ggctcccaac acc                                              23

<210> SEQ ID NO 10
<211> LENGTH: 19
<212> TYPE: DNA
<213> ORGANISM: Artificial, Natural, or Synthetic Sequence
<220> FEATURE:
<223> OTHER INFORMATION: Aggrecan Primer Forward Sequence

<400> SEQUENCE: 10
gctaccctga cccttcatc                                                   19

<210> SEQ ID NO 11
<211> LENGTH: 20
<212> TYPE: DNA
<213> ORGANISM: Artificial, Natural, or Synthetic Sequence
<220> FEATURE:
<223> OTHER INFORMATION: Aggrecan Primer Reverse Sequence

<400> SEQUENCE: 11
aagctttctg ggatgtccac                                                  20

<210> SEQ ID NO 12
<211> LENGTH: 24
<212> TYPE: DNA
<213> ORGANISM: Artificial, Natural, or Synthetic Sequence
<220> FEATURE:
<223> OTHER INFORMATION: Aggrecan Primer Probe Sequence

<400> SEQUENCE: 12
tgacgccatc tgctacacag gtga                                             24
```

DERMIS-DERIVED CELLS FOR TISSUE ENGINEERING APPLICATIONS

CROSS-REFERENCE TO RELATED APPLICATIONS

This application is a continuation-in-part of application Ser. No. 11/571,790 filed Jan. 8, 2007, which is a continuation of International Application No. PCT/US2005/24269 filed Jul. 8, 2005, which claims the benefit of U.S. Provisional Application Ser. No. 60/586,862 filed on Jul. 9, 2004; and also a continuation-in-part of International Application Nos. PCT/US2007/066089, PCT/US2007/066085, and PCT/US2007/066092 all filed Apr. 5, 2007, and all of which claim the benefit of U.S. Provisional Application Nos. 60/789,851, 60/789,853, and 60/789,855 all filed Apr. 5, 2006, all of which are incorporated herein by reference.

STATEMENT OF GOVERNMENT INTEREST

This invention was made with government support under Grant Number R01 AR47839-2 awarded by the National Institutes of Health. The government has certain rights in the invention.

SEQUENCE LISTING

This disclosure includes a sequence listing submitted as a text file pursuant to 37 C.F.R. §1.52(e)(v) named sequence listing.txt, created on Apr. 3, 2007, with a size of 2,809 bytes, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984). The symbols and format used for nucleotide and amino acid sequence data comply with the rules set forth in 37 C.F.R. §1.822.

BACKGROUND

Tissue engineering is an area of intense effort today in the field of biomedical sciences. The development of methods of tissue engineering and replacement is of particular importance in tissues that are unable to heal or repair themselves, such as articular cartilage. Articular cartilage is a unique avascular, aneural and alymphatic load-bearing live tissue, which is supported by the underlying subchondral bone plate. Articular cartilage damage is common and does not normally self-repair. Challenges related to the cellular component of an engineered tissue include cell sourcing, as well as expansion and differentiation. Findings of recent well-designed studies suggest that autologous chondrocyte implantation is the most efficacious technique for repairing symptomatic full-thickness hyaline articular cartilage defects, which engender a demand for cell-based strategies for cartilage repair. Further studies have also attempted to engineer cartilage via the combination of biodegradable or biocompatible scaffolds with differentiated chondrocytes. According to these studies, it is unlikely that a sufficient supply of differentiated chondrocytes will be available for clinical applications.

Numerous studies have focused on cell sources from tissues other than cartilage for cartilage tissue engineering. Embryonic stem (ES) cells represent a valuable source for this purpose. The application of ES cells in this area, however, is still limited particularly because of ethical considerations. A number of researchers have investigated various adult tissues including bone marrow, muscle, and adipose tissue as alternative cell sources for cartilage tissue engineering. However, autologous procurement of these tissues has potential limitations.

Skin is the largest organ in the body and is relatively easily accessible with minimal insult to the donor. The skin dermis is considered, therefore, one of the best autologous source organs to isolate stem/progenitor cells for future therapeutic applications not only in the replacement of skin, but also as an alternative cell source for several other organs outside of skin. Recently accumulating evidence indicates that skin dermis contains cells that can generate multiple lineages including neurons, glia, smooth muscle cells and adipocytes. Thus, cells from the skin dermis may prove to be a useful alternative cell source for articular cartilage tissue engineering. There is increasing evidence which suggests that human dermal fibroblasts cultured with demineralized bone powder acquire a chondroblast phenotype and express cartilage-specific matrix proteins. However, evidence shows that there are several types of fibroblasts in the skin dermis with different functions, which suggests the limitation of these cells. Although the existence of chondrogenic precursor cells in skin dermis has long been postulated, thus far it has been impossible to induce these heterogeneous cells to differentiate into chondrocytes exclusively, either in vivo or in vitro.

Previous studies using dermal fibroblasts showed that demineralized bone powder could induce the formation of colonies exhibiting a chondrocytic phenotype. However, no further evidence exists to show whether these chondroinduced cells can be considered to originate from stem cells, fully mature fibroblasts, or a dermal subpopulation of cells with latent chondrogenic potential. Although a number of researchers have investigated techniques to isolate subpopulations from the dermis for different purposes, none of these subpopulations has been isolated specifically for cartilage regeneration. Thus, there is an absence of well defined and efficient protocols for the selective isolation and proliferation of dermis-derived cells, followed by directing their differentiation into the chondrogenic lineage in vitro.

SUMMARY

The present disclosure, according to certain example embodiments, is generally in the field of improved methods for tissue engineering. More particularly, the present disclosure relates to methods for inducing differentiation of dermis-derived cells to serve as a source of chondrocytes and associated methods of use in the formation tissue engineered constructs. As used herein, a "construct" or "tissue engineered construct" refers to a three-dimensional mass having length, width, and thickness, and which comprises living mammalian tissue produced in vitro.

In certain embodiments, the present disclosure provides a modified rapid adhering process that involves purifying dermis-isolated, aggrecan sensitive (DIAS) cells for chondrogenic differentiation and allowing differentiated cells to self-assemble into a tissue engineering construct. Dermis derived cells are attractive since they provide autologous cells without causing complications at the donor site, due to the high regenerative capacity of skin. These cells can also be harvested with a low degree of invasiveness. The methods of the present disclosure are advantageous in preparing autologous cells to be transplanted to any patient for whom repair of damaged tissues by regeneration therapy will be needed. With regard to the availability of DIAS cells for clinical use, DIAS cells can be obtained with a low degree of invasiveness and without causing complications at the donor site due, to their high regenerative capacity. Thus, the methods of the present disclosure also provide therapeutic strategy that uses the self-assembly of chondroinduced DIAS cells to produce tissue in vitro for use as an autologous transplant in vivo.

Tissue engineered constructs formed by DIAS cells may exhibit cartilage specific ECM components throughout, while constructs formed using other dermis derived subpopulations often result in heterogeneous matrices. Thus, the methods of the present disclosure provide substantially homogeneous tissue engineered constructs. The methods of the present disclosure may reduce the likelihood of heterogeneous cell subpopulations spontaneously differentiating into divergent lineages and, in the case of fibroblasts, decreases the risk of fibrochondrocytic formation.

DRAWINGS

The patent or application file contains at least one drawing executed in color. Copies of this patent or patent application publication with color drawing(s) will be provided by the Office upon request and payment of the necessary fee.

Some specific example embodiments of the disclosure may be understood by referring, in part, to the following description and the accompanying drawings.

FIG. 1 shows a photomicrograph image of fibroblasts grown on 2.5 µg/cm² aggrecan-coated TCP surface. (A) Edge of the well (original magnification=10×). (B) Center of the well (original magnification 4×).

FIG. 2 shows a photomicrograph image of eosin stained aggrecan-coated TCP surface. (A) Schematic representation of a well. Panels B, C, D, and E show the center of the well. Panels F, G, H, and I show the edge of the well. (B, F) control; (C, G) 2.5 µg/cm²; (D, H) 5 µg/cm²; (E, I) 10 µg/cm².

FIG. 5 is a photomicrograph image showing aggrecan induced morphological changes in chondrocytes, DIAS cells and fibroblasts after 1 day in culture. (A) chondrocytes with aggrecan; (B) chondrocytes without aggrecan; (C) DIAS cells with aggrecan; (D) DIAS cells without aggrecan; (E) fibroblasts with aggrecan; (F) fibroblasts without aggrecan.

FIG. 6 is a photomicrograph image showing the detection of extracellular matrix of cartilage in DIAS cells after 1 day in culture. (A, B) Safranin-O stain for proteoglycans; (C, D) Immunohistological stain for collagen type II protein; (A, C) Aggrecan treated surface; (B, D) Without aggrecan treated surface.

FIG. 8 are graphs of the effect of aggrecan coated surfaces on collagen type I and type II expression of DIAS cells cultured for a period of 2 weeks. A) Collagen type I expression B) Collagen type II expression and C) Ratio of Collagen type II to collagen type I FIG. 9 shows fluorescent images illustrating organization of vinculin and F-actin in chondrocytes, DIAS cells and fibroblasts after 36 hrs. Vinculin was stained with Alexa 488 (green), F-actin was stained with rhodamine phalloidin (red), Nucleus was stained with DAPI (blue). (A, B, C, D, E, F) vinculin, (a, b, c, d, e, f) F-actin, Original magnification, 63×.

FIG. 10 is a graph of the collagen type I and II expression of DIAS cells cultured on tissue culture treated and non-tissue culture treated polystyrene, with or without aggrecan over a period of 14 days.

Figure 11:
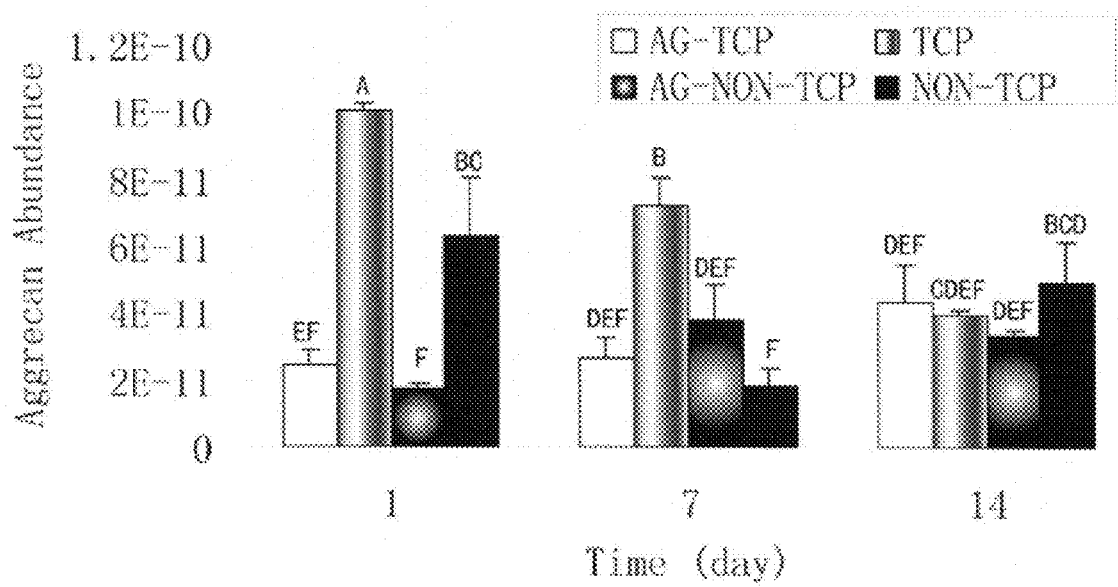

FIG. 11 is a graph of the effect of aggrecan on aggrecan expression of DIAS cells cultured on tissue culture and non-tissue culture treated polystyrene coated with or without aggrecan.

Figure 12:
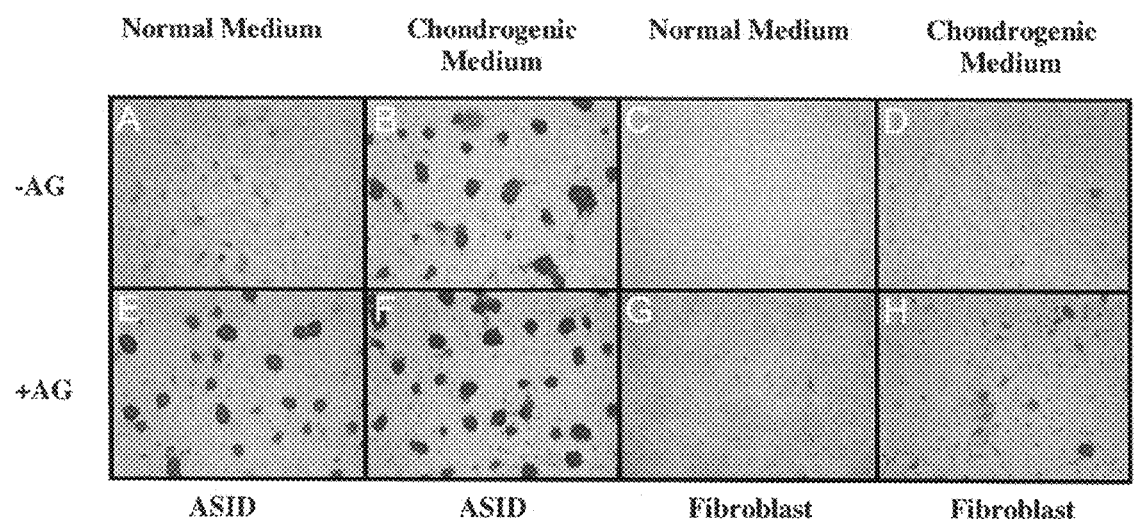

FIG. 12 is a photomicrograph image of the detection of proteoglycans in DIAS cells cultured in normal medium and chondrogenic medium at day 1. (A) DIAS cells cultured on non-tissue culture treated polystyrene with normal medium; (B) DIAS cells cultured on non-tissue culture treated polystyrene with chondrogenic medium; (C) Fibroblasts cultured on non-tissue culture treated polystyrene with normal medium; (D) Fibroblasts cultured on non-tissue culture treated polystyrene with chondrogenic medium; (E) DIAS cells cultured on aggrecan-coated non-tissue culture treated polystyrene with normal medium; (F) DIAS cells cultured on aggrecan-coated non-tissue culture treated polystyrene with chondrogenic medium; (G) Fibroblasts cultured on aggrecan-coated non-tissue culture treated polystyrene with normal medium; (H) Fibroblasts cultured on aggrecan-coated non-tissue culture treated polystyrene with chondrogenic medium; Original magnification=4×.

Figure 13:
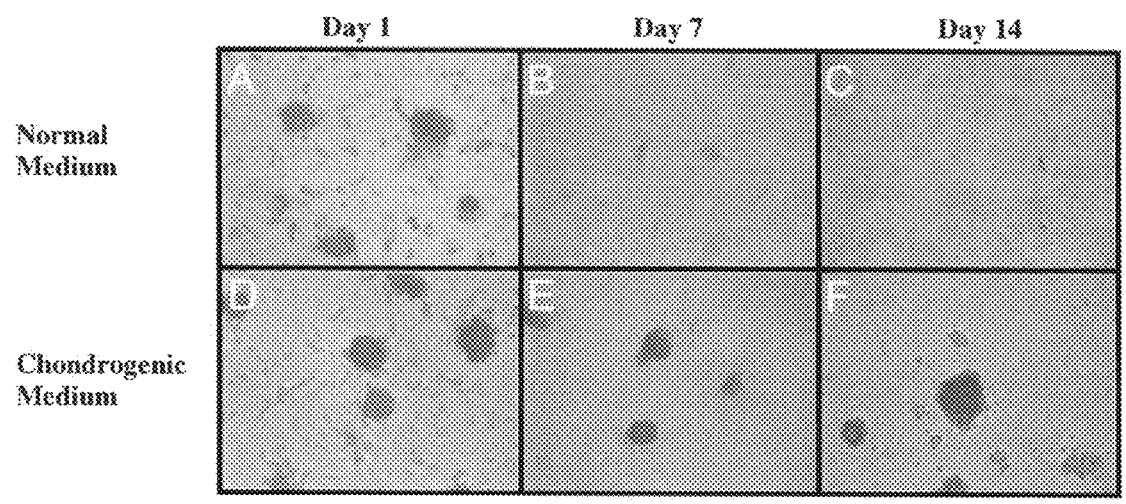

FIG. 13 is a photomicrograph image of the detection of proteoglycans in DIAS cells cultured in aggrecan-coated non-tissue culture treated polystyrene wells with normal medium and chondrogenic medium over a period of 14 days. (A) Normal medium at day 1; (B) Normal medium at day 7; (C) Normal medium at day 14; (D) Chondrogenic medium at day 1; (E) Chondrogenic medium at day 7; (F) Chondrogenic medium at day 14; Original magnification=10×.

Figure 14:
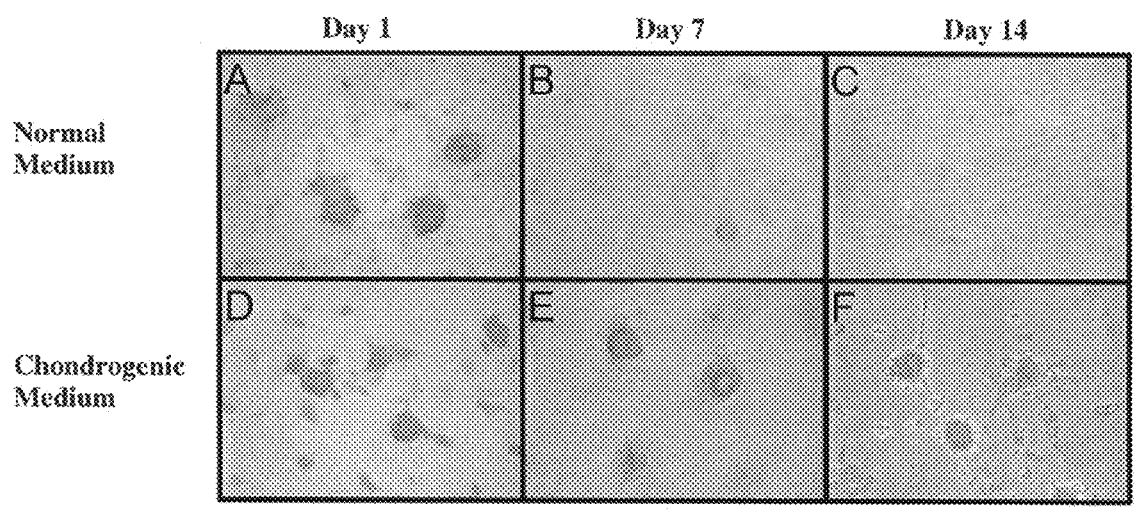

FIG. 14 is a photomicrograph of the detection of type II collagen in DIAS cells cultured on aggrecan-coated non-tissue culture treated polystyrene wells with normal medium and chondrogenic medium over a period of 14 days. (A) Normal medium at day 1; (B) Normal medium at day 7; (C) Normal medium at day 14; (D) Chondrogenic medium at day 1; (E) Chondrogenic medium at day 7; (F) Chondrogenic medium at day 14; Original magnification=10×.

FIG. 15 is a graph of the effect of aggrecan on collagen type I gene expression of DIAS cells and fibroblasts grown on non-tissue culture treated polystyrene with or without aggrecan coating over a period of 14 days.

FIG. 16 is a graph of the effect of aggrecan on cartilage oligomeric protein gene expression of DIAS cells and fibroblasts grown on non-tissue culture treated polystyrene with or without aggrecan coating over a period of 14 days.

FIG. 17 is a graph of the effect of aggrecan on aggrecan abundance (A) and aggrecan gene expression (B) of DIAS cells and fibroblasts grown on non-tissue culture treated polystyrene with or without aggrecan coating over a period of 14 days.

FIG. 18 is a graph of the detection of cartilage matrix protein collagen type II in DIAS cells and fibroblasts cultured on non-tissue culture treated polystyrene with or without aggrecan coating at day 1, 7 and 14.

Figure 19:
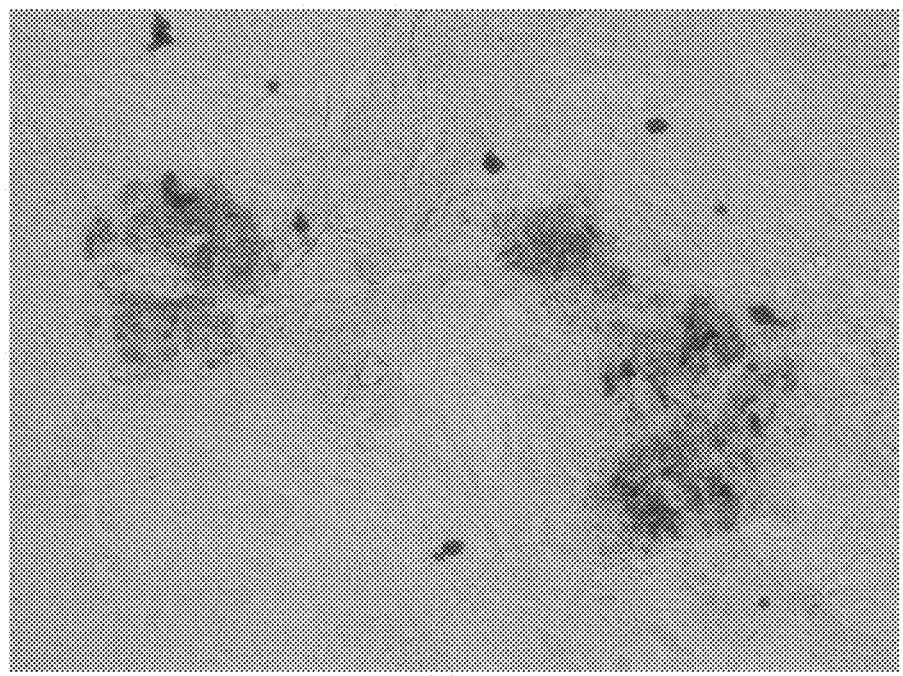

FIG. 19 is a photomicrograph image of oil red stain for differentiated DIAS cells after four weeks of culture.

Figure 20:
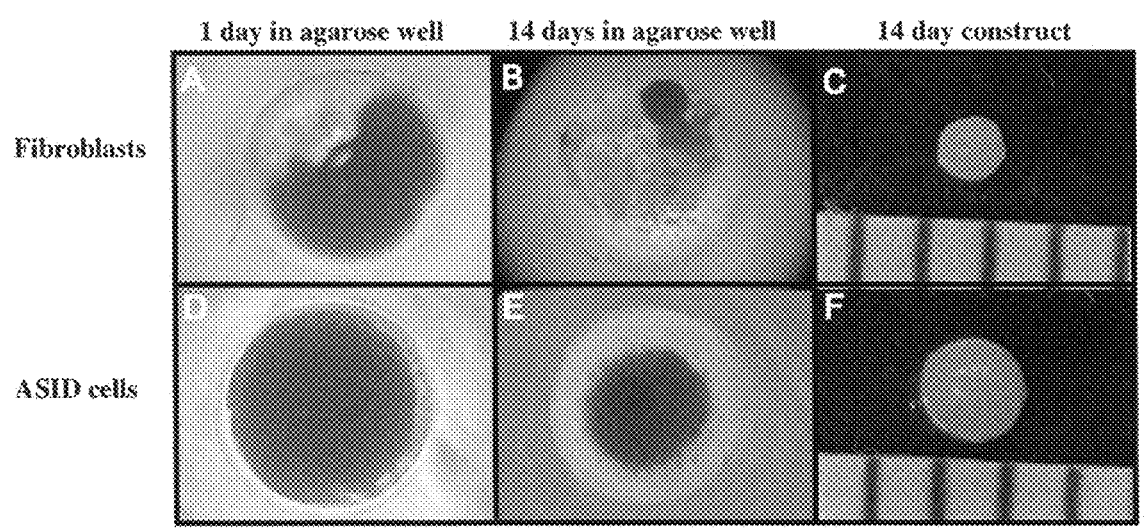

FIG. 20 is a photomicrograph image of constructs formed using self-assembly of DIAS cells and fibroblasts. (A) Fibroblasts grown in an agarose well for 1 day. (B) Fibroblasts grown in an agarose well for 14 days. (C) Construct formed by fibroblasts after culture for 14 days. (D) DIAS cells grown in an agarose well for 1 day. (E) DIAS cells grown in an agarose well for 14 days. (F) Construct formed by DIAS cells after culture for 14 days.

Figure 21:
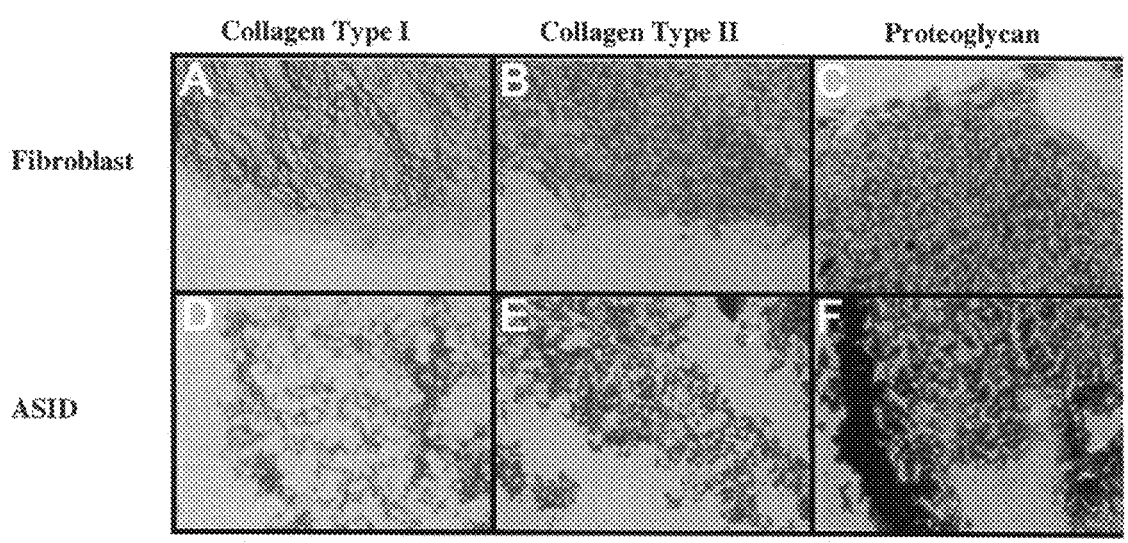

FIG. 21 is a photomicrograph image showing the detection of extracellular matrix of cartilage in constructs formed by DIAS cells and fibroblasts. (A, B, C) Fibroblasts; (D, E, F) DIAS cells; (A, D) Collagen type I stain; (B, E) Collagen type II stain; (C, F) Safranin-O stain.

Figure 22:
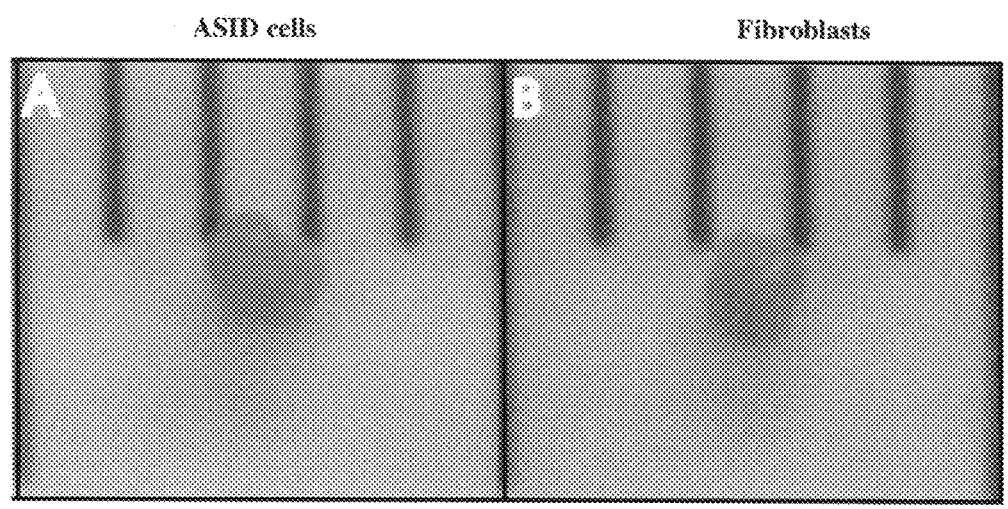

FIG. 22 is a photomicrograph image of constructs formed using self-assembly of DIAS cells and fibroblast cells after culture on aggrecan-coated non-tissue culture treated polystyrene for a period of 14 days.

Figure 23:
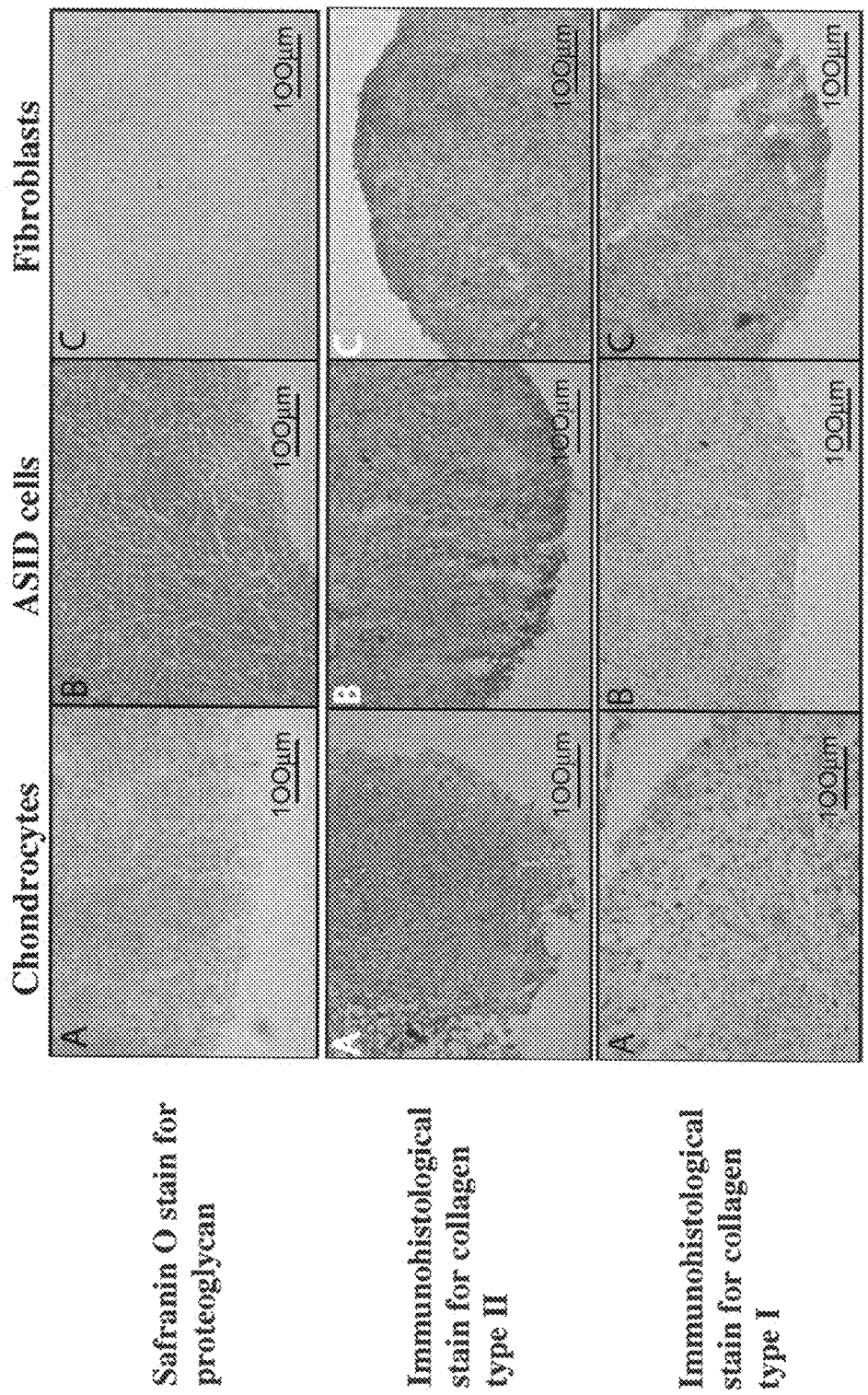

FIG. 23 is a photomicrograph image showing the detection of cartilage specific extracellular matrix in constructs self-assembled by (A) chondrocytes, (B) DIAS cells, and (C) fibroblasts. All were cultured on aggrecan-coated non-tissue culture treated polystyrene for 14 days.

Figure 24:
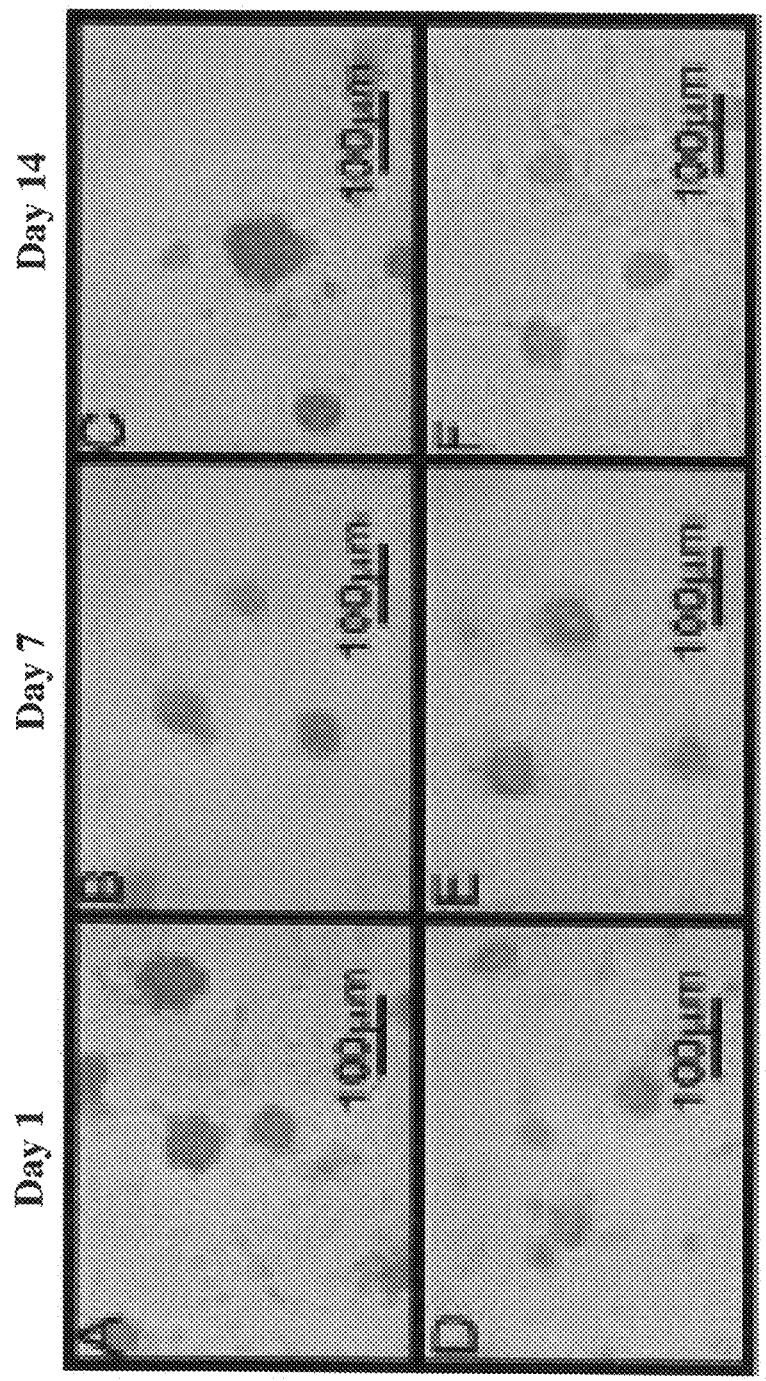

FIG. 24 shows detection of cartilage-specific extracellular matrix DIAS cells cultured for 1-14 days on aggrecan-coated surfaces. Using Safranin-O, all nodules stained positively for glycosaminoglycans (GAGs) (A-C). Immunohistologic staining was positive for type II collagen (Col II) (D-F), which is evidence of chondrocytic nodule formation.

Figure 25:
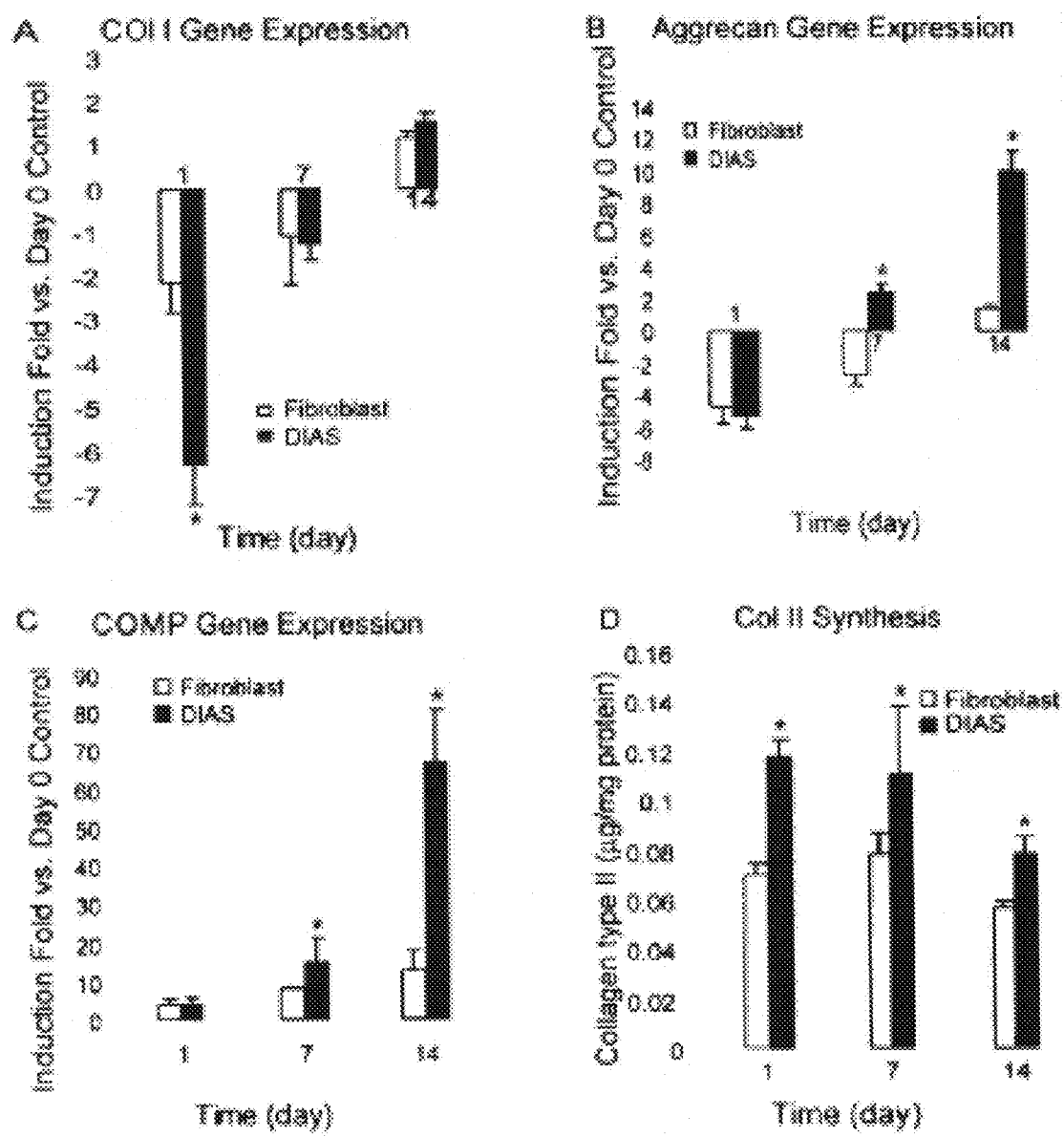

FIG. 25 shows expression and synthesis of cartilage specific markers in DIAS cells compared with fibroblasts. Reverse transcriptase-polymerase chain reaction results showed significant inhibition of type I collagen (Col I) gene expression for 1-7 days in both cell populations (A). On aggrecan coated surfaces (ACS), aggrecan and cartilage oligomeric protein (COMP) gene expression was significantly increased in DIAS cells compared with fibroblasts on days 7 and 14 (B and C). Enzyme linked immunosorbent assay showed that aggrecan coating of surfaces resulted in higher levels of type II collagen in DIAS cell cultures than in fibroblast cultures (D) at every time point tested. These data suggest that the extent of chondroinduction undergone DIAS cells when exposed to ACS is significantly greater than that undergone by fibroblasts. Values are the mean and SD. *=$P<0.05$ versus fibroblasts.

Figure 26:
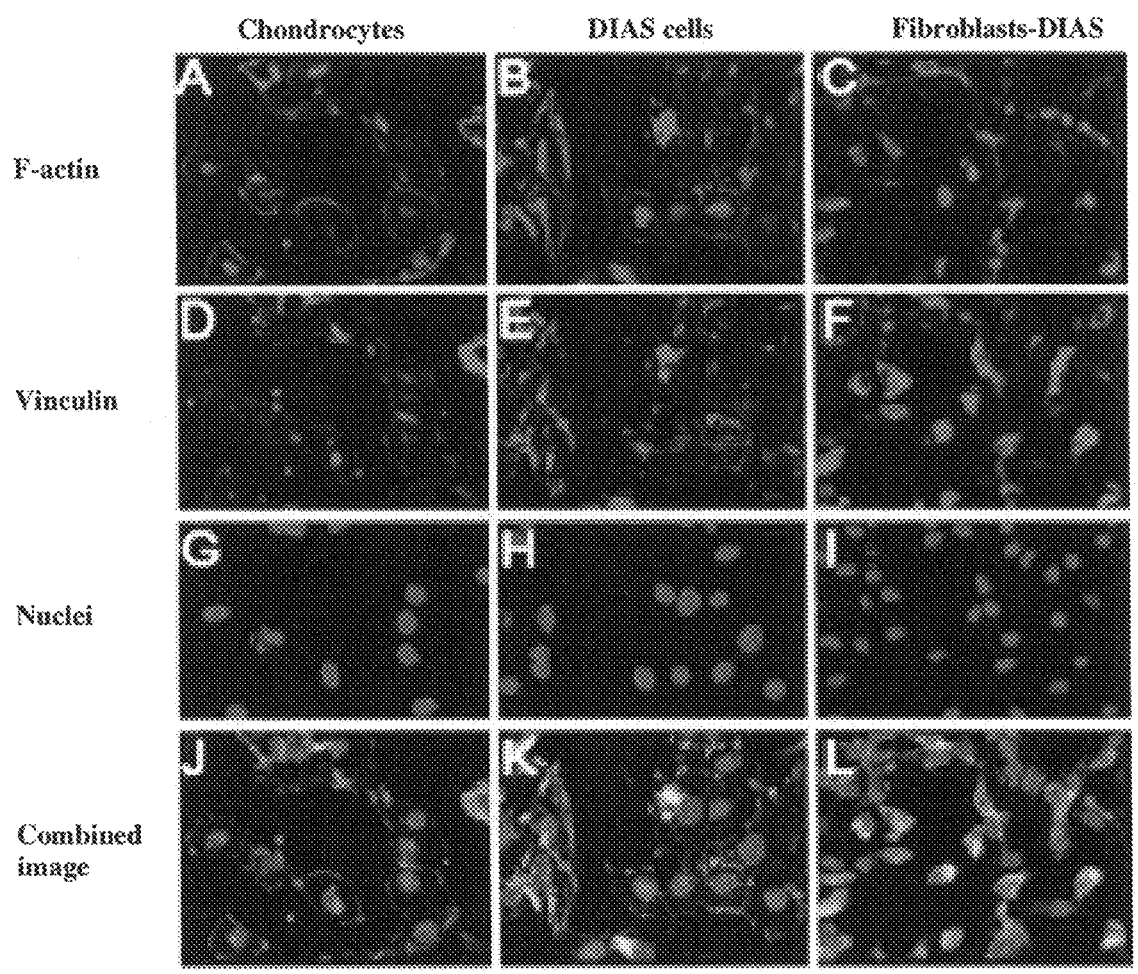

FIG. 26 shows reorganization of filamentous actin (F-actin) and vinculin in chondrocytes, DIAS cells, and fibroblasts after 36 hours of monolayer culture on aggrecan-coated surfaces. F-actin was stained with rhodamine and phalloidin (red) (A-C). Vinculin was stained with Alexa Fluor 488 (green) (D-F). Nuclei were stained with 4',6 diamidino-2-phenylindole (blue) (G-I). A punctated distribution of F-actin was seen at the periphery of chondrocytes (A) and DIAS cells (B), while a dense collection of F-actin was seen throughout the fibroblasts (C). The organization of vinculin mirrored that of F-actin in each group. Combined images with all 3 stains were also created (J-L). On uncoated control surfaces, the 3 cell groups exhibited similar F-actin and vinculin distribution (results not shown). (Original magnification×63.)

Figure 27:
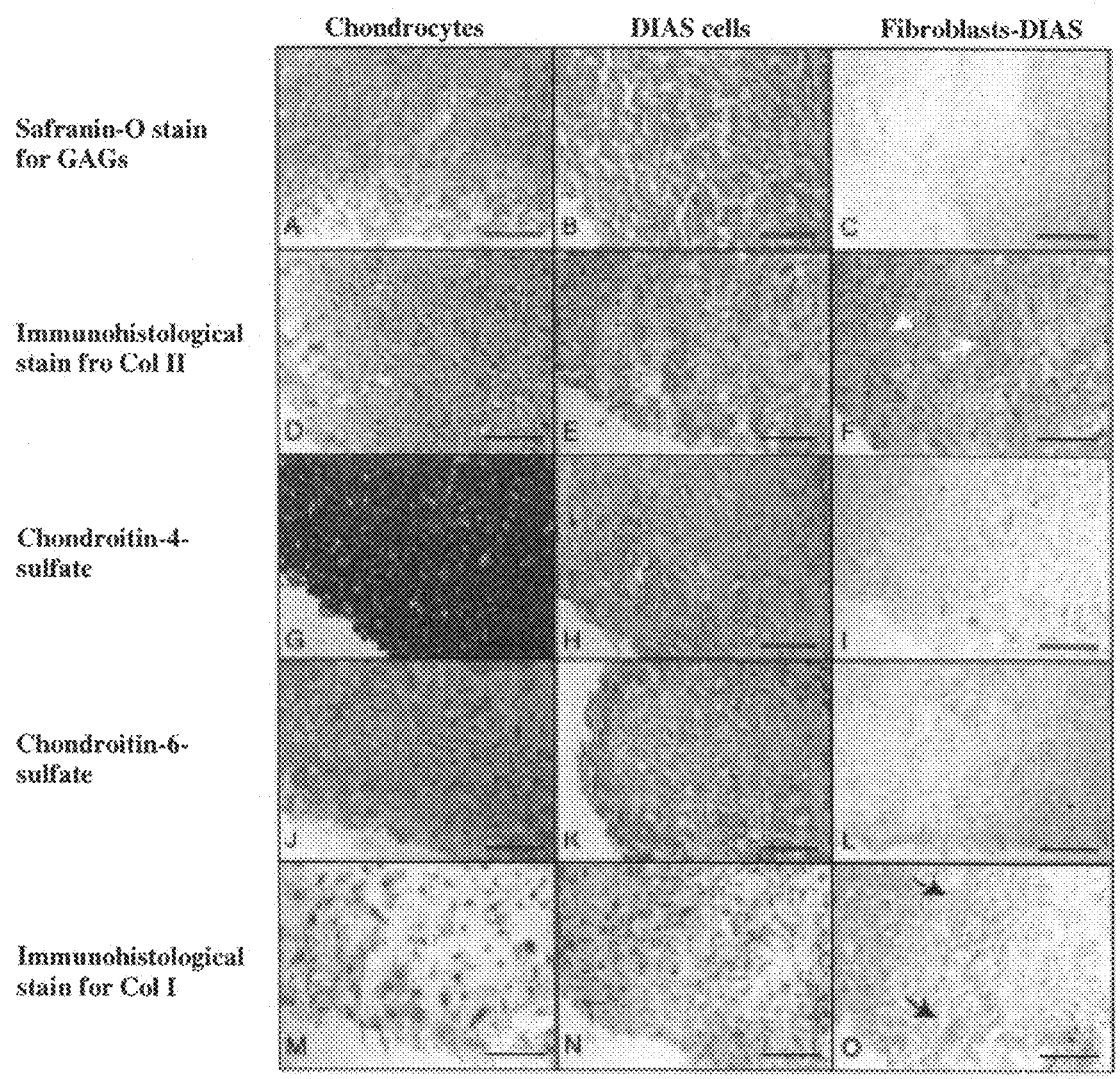

FIG. 27 shows detection of cartilage specific extracellular matrix (ECM) in constructs self-assembled for 2 weeks using chondrocytes, DIAS cells, and floating DIAS (F-DIAS) cells. Sections taken from chondrocyte constructs were stained for glycosaminoglycans (GAGs) (A), type II collagen (Col II) (D), chondroitin 4-sulfate (G), chondroitin 6-sulfate (J), and type I collagen (M). Spherical chondrocytes were noted within a matrix containing GAGs, type II collagen, chondroitin 4-sulfate, and chondroitin 6-sulfate, indicative of cartilage formation. DIAS constructs also stained positively for the same cartilage specific ECM (B, E, H, and K). Type I collagen was not observed within chondrocyte or DIAS constructs (M and N). In contrast, constructs from F-DIAS cells exhibited negligible GAG staining (C), poor type II collagen staining (F) (arrows) poor chondroitin 4-sulfate staining (I), and negligible chondroitin 6-sulfate staining (L), while staining for type I collagen (O) (arrows) was observed. Bars=50 μm.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The methods of the present disclosure generally comprise providing aggrecan sensitive isolated dermis cells and seeding the cells onto an aggrecan coated surface. The term "aggrecan sensitive isolated dermis cells" or "DIAS cells" as used herein refers to any plastic rapidly adhering subpopulation of skin cells that are capable of chondrogenic differentiation when cultured on aggrecan. The term "chondrogenic differentiation" as used herein refers to any process that would result in cells that produce glycosaminoglycans and collagen type II. The term "construct" or "tissue engineered construct" as used herein refers to a three-dimensional mass having length, width, and thickness, and which comprises living mammalian tissue produced in vitro. As used herein, "self-assemble" or "self-assembly" as used herein refers to a process in which specific local interactions and constraints between a set of components cause the components to autonomously assemble, without external assistance, into the final desired structure through exploration of alternative configurations.

Chondrogenic Differentiation of Dermis-Derived Cells

The DIAS cells used in conjunction with the methods of the present disclosure are fibroblastic cells. DIAS cells are a subpopulation of dermis derived fibroblastic cells that may be characterized by their fast attachment to the bottom surface of a culture flask and have the potential for chondrogenic differentiation when seeded on aggrecan-coated surfaces. Aggrecan has been found to play an essential role in the chondrogenesis process and the subsequent maintenance of the chondroncyte phenotype in vivo. Seeded or chondroinduced DIAS cells are phenotypically, morphologically, and functionally similar to chondrocytes.

DIAS may be derived from the dermis layer of the skin using methods known in the art. The cells are generally derived from an autologous source so as to avoid biocompatibility issues. After isolation of the cells from the source, the cells may be cultured to form a homogenous culture of cells. In some embodiments, to obtain a homogenous culture of DIAS cells, the cells may be isolated using enzymatic digestion. Following isolation, in some embodiments, the cells may be purified using density gradient separation or by allowing the cells to attach to a surface of a substrate for a defined period of time and subsequently removing any cells which do not attach within the defined period of time.

To induce chondrogenic differentiation, homogenous cultured DIAS cells may be seeded on aggrecan coated surfaces (ACS). The aggrecan may be coated on the ACS at a concentration of about 0.1 to about 100 μg/cm² of well surface, for example, aggrecan may be coated at a concentration of about 1 to about 50 μg/cm², or at a concentration of about 10 μg/cm² of well surface. For example, 2×10⁵ cells in culture medium may be seeded per well in 24 well plates coated with aggrecan (bottom well area approximately 2 cm²). Other coatings also may be included. For example the ACS also may include keratin sulfate, chondroitin sulfate, and hyaluronate. Generally, the cells may be cultured on the ACS for a period of about seven days. To verify that chondrogenic differentiation has occurred, differentiation assays may be performed to detect the presence of chondrocyte-specific extracellular matrix. For example, the presence of cartilage markers, such as proteoglycans and collagen type II may be detected using methods known to those of ordinary skill in the art. In other embodiments, cartilage specific matrix gene expression may be evaluated using methods currently known in the art. For example, the cells may be assessed by semiquantitative RT-PCR analysis to determine the expression of cartilage specific matrix genes.

Hydrogel Coating of Culture Vessels

The culture vessels may be coated with hydrogel in conjunction with the methods of present disclosure. "Hydrogel" as used herein refers to a colloid in which the particles are in the external or dispersion phase and water is in the internal or dispersed phase. Generally, suitable hydrogels are non-toxic to the cells, are non-adhesive, do not induce chondrocyte attachment, allow for the diffusion of nutrients, do not degrade significantly during culture, and are firm enough to be handled.

In certain embodiments, the bottoms and sides of well plates may be coated with 2% agarose (w/v). While 2% agarose is used in certain embodiments, in other embodiments, the agarose concentration may be in the range of about 0.5% to about 4% (w/v). The use of lower concentrations of agarose offers the advantage of reduced costs; however, at concentrations below about 1% the agarose does not stiffen enough for optimal ease of handling. As an alternative to agarose, other types of suitable hydrogels may be used, such as, for example, alignate and polyHEMA.

Self-Assembly of Chondrogenically Induced DIAS Cells

The chondrogenically induced DIAS cells are seeded on hydrogel coated culture vessels and allowed to self-assemble. For example, 4.8×10⁶ chondrogenically induced DIAS cells in medium may be seeded per well in 24 well plates (bottom well area approximately 2 cm²). The chondrogenically induced DIAS cells are allowed to self-assemble on the hydrogel coated culture vessel. The self-assembly may result in the formation of non-attached constructs on the hydrogel surfaces. It is preferable to use hydrogel coated culture vessels instead of tissue culture treated surfaces since articular chondrocytes seeded onto standard tissue culture treated plastic (TCP) readily attach, spread, and dedifferentiate.

In certain embodiments, the self-assembly process may occur in culture vessels that are shaken continuously on an orbital shaker and then pressurized.

In certain embodiments, the pressurization of the cells may occur in a pressure chamber. Pressurization of the samples during the self-assembly process may aid in increased extracellular matrix synthesis and enhanced mechanical properties. In certain embodiments, the cells may be pressurized to 10 MPa at 1 Hz using a sinusoidal waveform function. In other embodiments, the cells may be pressurized during self-assembly of the cells.

In particular embodiments, a loading regimen (e.g. compressive, tensile, shear forces) may be applied to the cells during self-assembly based on physiological conditions of the native tissue in vivo. Loading of the cells during self-assembly and/or construct development may cause enhanced cartilage specific gene expression and protein expression in the constructs.

In particular embodiments, the cells may be treated with staurosporine, a protein kinase C inhibitor and actin disrupting agent, during the self-assembly process to reduce synthesis of αSMA, a contractile protein. Reducing αSMA in the constructs via staurosporine treatment may reduce construct contraction and may also upregulate ECM synthesis. In general, the cells, constructs or both may be treated with staurosporine or a Rho-associated kinase "ROCK" inhibitor or both.

In other embodiments, the cells may be treated with growth factors to increase construct growth and matrix synthesis. Suitable examples of growth factors that may be used with the methods of the present disclosure include, but are not limited to, TGF-β1 and IGF-I. The dosing of the growth factors may be intermittent or continuous throughout the period of the self-assembly process. One of ordinary skill in the art, with the benefit of this disclosure, will be able to determine the appropriate dosing regimen and amount and type of growth factor to provide to the developing constructs. In general, the cells, constructs or both may be treated with one or more growth factors, including TGF-beta 1, TGF-beta 3, BMP-2, BMP-4, and IGF-I.

Hydrogel Molds

In certain embodiments, the chondrogenically induced DIAS cells may be seeded on a hydrogel coated culture vessel, allowed to self-assemble into a tissue engineered construct, and molded into a desired shape. The self-assembly of the cells into a construct may occur on hydrogel coated culture vessels for about 1 to about 7 days before being transferred to a shaped hydrogel negative mold for molding the construct into the desired shape. In some embodiments, the desired shape may be in the shape of at least a portion of a joint, cartilaginous tissue of a mammal, tendon tissue of a mammal, or ligament tissue of a mammal. In other embodiments, the desired shape may be in the shape of at least a portion of a femur or a temporomandibular joint.

Alternatively, rather than seeding the chondrogenically induced DIAS cells on a hydrogel coated culture vessel, in certain embodiments, the cells may be seeded directly onto a shaped hydrogel negative mold. The shaped hydrogel negative mold may comprise agarose. Other non-adhesive hydrogels, e.g. alignate, may be used in conjunction with the methods of the present disclosure. In other embodiments, the hydrogel mold may be a two piece structure comprising, a shaped hydrogel negative mold and a shaped hydrogel positive mold. The shaped hydrogel negative and positive molds may comprise the same non-adhesive hydrogel or may be a comprised of different non-adhesive hydrogels.

In certain embodiments, the cells may be seeded on a hydrogel coated culture vessel and allowed to self-assemble into a construct. The construct may be transferred to a shaped hydrogel negative mold. A shaped hydrogel positive mold may be applied to the negative mold to form a mold-construct assembly. The mold-construct assembly may then further be cultured. As used herein, the term "mold-construct assembly" refers to a system comprising a construct or cells within a custom-shaped positive and a shaped negative hydrogel mold.

In certain embodiments, the molds may be shaped from a 3-D scanning of a total joint to result in a mold fashioned in the shape of said joint. In other embodiments, the molds may be shaped from a 3-D scanning of the ear, nose, or other non-articular cartilage to form molds in the shapes of these cartilages. In certain embodiments, the mold may be shaped to be the same size as the final product. In other embodiments, the molds may be shaped to be smaller than the final product. In certain embodiments, the molds may be fashioned to a portion of a joint or cartilage so that it serves as a replacement for only a portion of said joint or cartilage.

Other examples of shaped hydrogel molds and methods of developing scaffoldless tissue engineered constructs that may be useful in conjunction with the methods of the present disclosure may be found in co-pending application entitled "A Shape-Based Approach for scaffoldless Tissue Engineering," the disclosure of which is incorporated by reference herein.

Analysis of the Constructs

The properties of constructs may be tested using any number of criteria including, but not limited to, morphological, biochemical, and biomechanical properties, which also may be compared to native tissue levels. In this context, morphological examination includes histology using safranin-O and fast green staining for proteoglycan and GAG content, as well as picro-sirius red staining for total collagen, immunohistochemistry for collagens I and II, and confocal and scanning electron microscopies for assessing cell-matrix interactions. Biochemical assessments includes picogreen for quantifying DNA content, DMMB for quantifying GAG content, hydroxyproline assay for quantifying total collagen content, and ELISA for quantifying amounts of specific collagens (I and II), and RT-PCR for analysis of mRNA expression of proteins associated with the extracellular matrix (e.g. collagen and aggrecan).

Constructs also may be evaluated using one or more of incremental tensile stress relaxation incremental compressive stress relaxation, and biphasic creep indentation testing to obtain moduli, strengths, and viscoelastic properties of the constructs. Incremental compressive testing under stress relaxation conditions may be used to measure a construct's compressive strength and stiffness. Incremental tensile stress relaxation testing may be used to measure a construct's tensile strength and stiffness. Additionally, indentation testing under creep conditions may be used to measure a construct's modulus, Poisson's ratio, and permeability.

Without wishing to be bound by theory or mechanism, although both collagen II and GAG are excellent predictors of biomechanical indices of cartilage regeneration, typically only collagen II exhibits a positive correlation. Though seemingly this hypothesis is counterintuitive for compressive properties, as GAG content is usually thought to correlate positively with compressive stiffness, our results show that in self-assembled constructs, GAG is negatively correlated with the aggregate modulus ($R^2=0.99$), while collagen II is positively correlated ($R^2=1.00$).

The constructs of the present disclosure may be assessed morphologically and/or quantitatively. Quantitatively, the constructs of the present disclosure may be evaluated using a functionality index (FI) as described in Eq. 1. The functionality index is an equally weighted analysis of ECM production and biomechanical properties that includes quantitative results corresponding to the constructs' salient compositional characteristics (i.e., amounts of collagen II and GAG) and biomechanical properties (compressive and tensile moduli and strengths).

$$FI = \frac{1}{4}\left(\left(1 - \frac{(G_{nat} - G_{sac})}{G_{nat}}\right) + \left(1 - \frac{(C_{nat} - C_{sac})}{C_{nat}}\right) + \right.$$

Eq. (1)

-continued
$$\frac{1}{2}\left(1 - \frac{(E^T_{nat} - E^T_{sac})}{E^T_{nat}}\right) + \frac{1}{2}\left(1 - \frac{(E^C_{nat} - E^C_{sac})}{E^C_{nat}}\right) +$$
$$\left. \frac{1}{2}\left(1 - \frac{(S^T_{nat} - S^T_{sac})}{S^T_{nat}}\right) + \frac{1}{2}\left(1 - \frac{(S^C_{nat} - S^C_{sac})}{S^C_{nat}}\right)\right)$$

In this equation, G represents the GAG content per wet weight, C represents the collagen II content per wet weight, $E^T$ represents the tensile stiffness modulus, $E^C$ represents the compressive stiffness modulus, $S^T$ represents the tensile strength, and $S^C$ represents the compressive strength. Each term is weighted to give equal contribution to collagen, GAG, tension, and compression properties. The subscripts nat and sac are used to denote native and self-assembled construct values, respectively. The aggregate modulus is not used in Eq. 1, as it is expected to mirror the compressive modulus obtained from incremental compressive stress relaxation. Similarly, the amount of collagen I is not be used in Eq. 1, as this type of collagen may not appear in a measurable fashion; however, if the amount of collagen I is non-negligible, FI may be altered accordingly to account for it.

Each term grouped in parentheses in Eq. 1 calculates how close each construct property is with respect to native values, such that scores approaching 1 denote values close to native tissue properties. Equal weight is given to GAG, collagen II, stiffness (equally weighted between compression and tension), and strength (also equally weighted between compression and tension). This index, FI, will be used to assess the quality of the construct compared to native tissue values, with a lower limit of 0 and an unbounded upper limit, with a value of 1 being a construct possessing properties of native tissue. However, the FI can exceed 1 if optimization results in constructs of properties superior to native tissue.

Methods of Using the Tissue Engineered Constructs

A hydrogel coated culture vessel or shaped hydrogel negative mold is seeded with chondrogenically induced DIAS cells to produce new tissue, such as tissue of the knee meniscus, tendons, and ligaments. The hydrogel coated culture vessel or shaped hydrogel negative mold is typically seeded with cells; the cells are allowed to self-assemble to form a tissue engineered construct. In certain embodiments, applications of the tissue engineered construct include the replacement of tissues, such as cartilaginous tissue, the knee meniscus, joint linings, the temporomandibular joint disc, tendons, or ligaments of mammals.

The constructs may be treated with collagenase, chondroitinase ABC, and BAPN to aid in the integration of the constructs with native, healthy tissue surrounding the desired location of implantation. The integration capacity of a construct with native tissue is crucial to regeneration. A wound is naturally anti-adhesive, but debridement with chondroitinase ABC and/or collagenase removes anti-adhesive GAGs and enhances cell migration by removing dense collagen at the wound edge. BAPN, a lysyl oxidase inhibitor, may cause the accumulations of matrix crosslinkers and may, thus, strengthen the interface between the construct and native tissue at the desired location of implantation.

The tissue engineered constructs may be implanted into a subject and used to treat a subject in need of tissue replacement. In certain embodiments, the constructs may be grown in graded sizes (e.g. small, medium, and large) so as to provide a resource for off-the-shelf tissue replacement. In certain embodiments, the constructs may be formed to be of custom shape and thickness. In other embodiments, the constructs may be devitalized prior to implantation into a subject.

To facilitate a better understanding of the present disclosure, the following examples of specific embodiments are given. In no way should the following examples be read to limit or define the entire scope of the invention.

EXAMPLES

DIAS Cell Culture Conditions

Examples of constructs of the present disclosure were prepared using adult goat skins from 5 animals. The skins were separated from underlying adipose tissue using sterile scissors, washed in sterile phosphate-buffered saline (PBS) and cut into small pieces (1×1 cm$^2$). The skin tissue was then digested with 0.5% dispase in 4° C. overnight and then fixed onto a sterile plate, with the epidermis upward. The epidermis was removed by scraping with a blade and the dermis was meticulously cleaned to remove all adipose tissue and blood coagulates in vessels. The dermis was washed three times in sterile PBS, and minced into small pieces (2-3 mm$^2$), and digested in PBS solution containing 200 U/ml collagenase type II (Worthington, Lakewood, N.J.) at 37° C. for 15 h under gentle shaking conditions. After incubation, the cell suspension was suspended in Dulbecco's modified Eagle's medium (Gibco) containing 10% fetal bovine serum, 1% penicillin-streptomycin (Gibco/Invitrogen, Carlsbad, Calif.) and 1% fungizone (Gibco/Invitrogen) and centrifuged at 1,200 rpm for 5 min at room temperature. The supernatant was aspirated away. Cells were resuspended in cell culture medium and seeded in flasks. Media changes were performed every 3-4 days. After cells reached confluency, cells were treated with 0.5% dispase for 15 minutes, and the floating cells were discarded. Then, after cultured for 3 days, cells were harvested as normal fibroblast and passaged using a solution containing 0.25% trypsin and 5 mM EDTA (Sigma).

To obtain a homogeneous culture of DIAS cells, harvested cells were seeded in a tissue culture treated flask and allowed to attach for 10 min, after which the floating cells were discarded. The remaining cells were washed 3 times with PBS and continued to be cultured in culture medium.

To induce chondrogenic differentiation, 24 well tissue culture treated plates were coated with aggrecan at a concentration of 10 μg/cm$^2$. Wells were rinsed with PBS prior to plating. DIAS cells of passage 2 were plated at a concentration of 2×10$^5$ cells/well in 0.3 ml of medium. After 24 hrs, 0.7 ml medium was added in each well to reach a final volume of 1 ml. Triplicate samples from either control tissue culture plates or aggrecan-coated plates were collected at 24 hrs, 1 wk and 2 wk time points. Tissue culture treated 24 well plates without aggrecan were used as control. Chondrocytes and fibroblasts were used as a standard for comparison. Differentiation assays were then performed to detect chondrogenic differentiation.

Assessment of Aggrecan Coating of Well Surface on Fibroblast Morphology

Figure 1A:
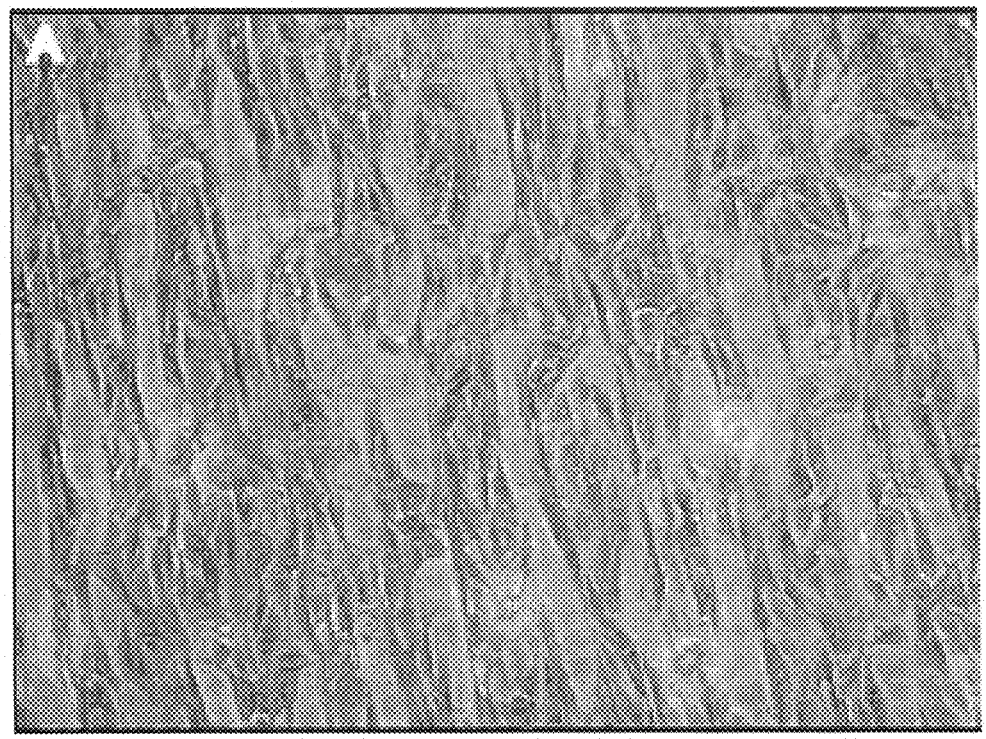
Figure 1B:
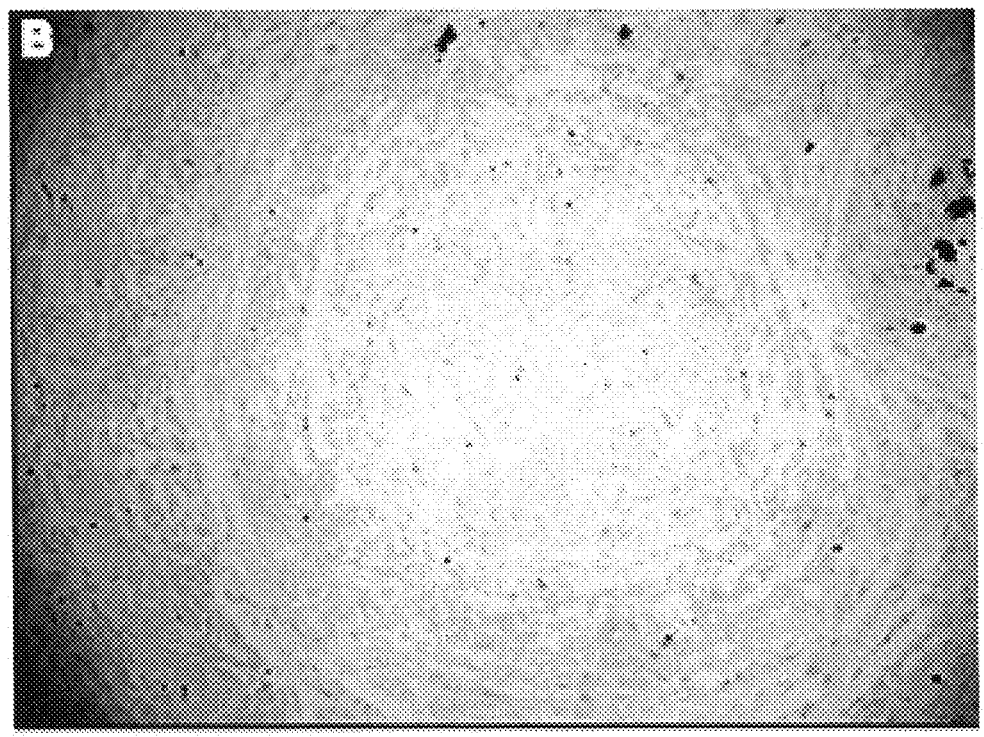

The effects of an aggrecan-coated surfaces on fibroblast morphology and organization were studied 24 hours after seeding. Cells grown on tissue culture treated polystyrene showed random cell orientation (data not shown), while cells grown on aggrecan-coated surfaces were oriented following a circular pattern (FIG. 1). To understand the circle-like fashion of fibroblasts grown on aggrecan-coated surface, the distribution of aggrecan on TCP surfaces was then investigated.

For aggrecan distribution test, 24 well plates were coated with different concentrations of aggrecan (2.5 μg/cm$^2$, 5 μg/cm$^2$ and 10 μg/cm$^2$). After aggrecan-coating, wells were stained with eosin for 1 min and washed with water twice. Negative control surface was pre-coated with water. Well surface were photographed using a Nikon CoolPix 990 digital camera mounted on a Nikon Eclipse TS-100 inverted microscope.

As shown in FIG. 2, the data illustrated that the aggrecan-coated surfaces formed micropatterned templates (parallel ridge/groove type structures) compared to the tissue culture treated control. Furthermore, the ridge width of these grooves increased with the increase of aggrecan concentration, while groove width decreased. The highest coating density resulted in grooves with ridge width/groove width of about 100-200/1-10 μm in aggrecan 10 g/cm$^2$ groups.

The data suggested an optimal concentration of aggrecan (10 μg/cm$^2$) for subsequent experiments. The choice was based on the observation that at this concentration there was wider aggrecan coverage on the surface of aggrecan (10 g/cm$^2$). It is expected that the nature of the conditioning biomolecules (in this case, aggrecan) and their position on the surface will have direct consequences on the recruitment, attachment, proliferation and differentiation of cells.

Figure 4A:
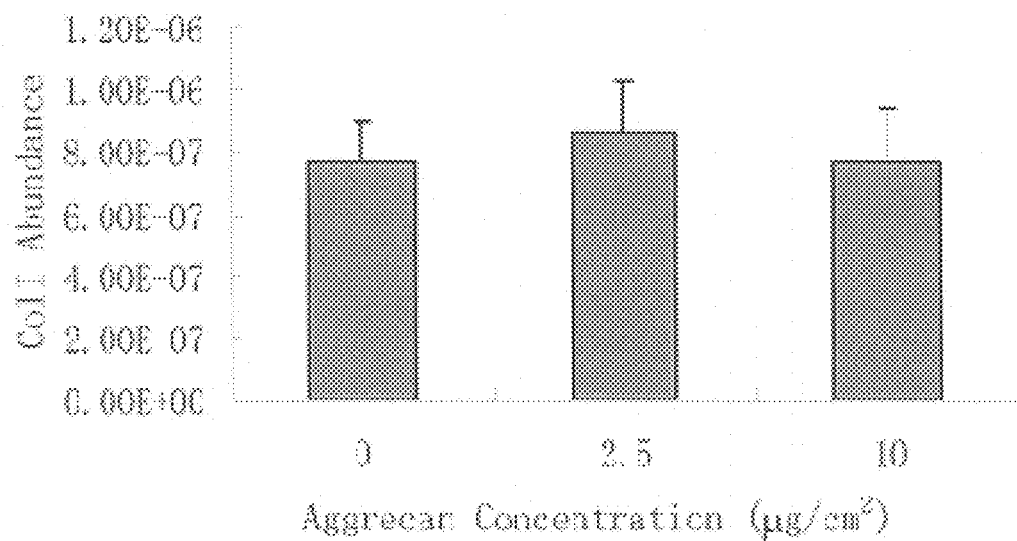
FIG. 4 is a graph of the effect of different aggrecan concentrations on the expression of collagen type I and II in DIAS cells. (A) Collagen type I (B) Collagen type II.

Aggrecan is highly negatively-charged and functions to bind and organize water molecules and repel negatively charged molecules within the articular cartilage. In addition, the aggrecan molecule is too large and immobile to redistribute itself, thus the addition of water causes aggrecan-rich matrix network to swell and expand, and results in substrate topography variation as well as surfaces charge variation in vivo. Based on these in vivo characteristics of aggrecan, it was hypothesized that aggrecan can be used as a specific ECM molecule to coat TCP surfaces for DIAS cells to chondrogenically differentiate. After aggrecan coating, it was found that aggrecan molecules deposit on TCP surfaces and orient into special grooves. These grooves can be detected by staining with eosin, an acid dye that normally has an affinity for positively charged components (FIG. 2). Also, the ridge dimensions of these aggrecan grooves show a dose-dependent increase, which implies a topography change might happen on TCP surfaces (FIGS. 2G, H and I). The results revealed that aggrecan-coated surfaces could supply a modified surface with specific topography, charge density and/or chemical composition for cells to attach. FIGS. 4A and B show the effect of different aggrecan concentration on the expression of collagen type I and II in DIAS cells, further suggesting an optimal concentration of aggrecan of 10 μg/cm$^2$.

Chondrogenic Differentiation in Mono-layer Culture

For differentiation assays, 24 well tissue culture treated plates were coated with aggrecan at a concentration of 10 μg/cm$^2$. Wells were rinsed with PBS prior to plating. Then, chondrocytes, DIAS cells and fibroblasts of passage 2 were plated at a concentration of 2×10$^5$ cells/well in 0.3 ml of medium. After 24 hrs, 0.7 ml medium was added in each well to reach a final volume of 1 ml. Triplicate samples from either control tissue culture treated plates or aggrecan-coated plates were collected at 24 hrs, 1 wk and 2 wk time points. Tissue culture treated 24 well plates were used as control.

To evaluate the chondrogenic differentiation percentage of fibroblast and DIAS cells, the aggrecan treated samples were compared after 24 hrs according to their chondrocytic nodules formation. FIG. 5 shows aggrecan induced morphological changes in chondrocytes, DIAS cells, and fibroblasts after 1 day in culture. Fibroblasts plated on tissue culture treated plastic alone attached to the surface, elongated, and spread to become spindle-shaped cells, maintaining a fibroblastic appearance. The majority of fibroblasts were shown to align strictly along the direction of the ridges/grooves formed by aggrecan. In sharp contrast, DIAS cells grown on aggrecan-coated surfaces appeared to be small, round cells suspended in culture medium when first plated. After one day in culture on aggrecan, DIAS cells were displaying rounded morphology aggregates. FIG. 5E shows that different dimensions of the ridge/groove patterns only affected fibroblast distribution. All concentrations of aggrecan induced different degrees of directional migration of fibroblasts with the growing direction aligning the microgrooves. However, the wider microgrooves seemed to trap more fibroblast than the narrow ones.

Figure 3A:
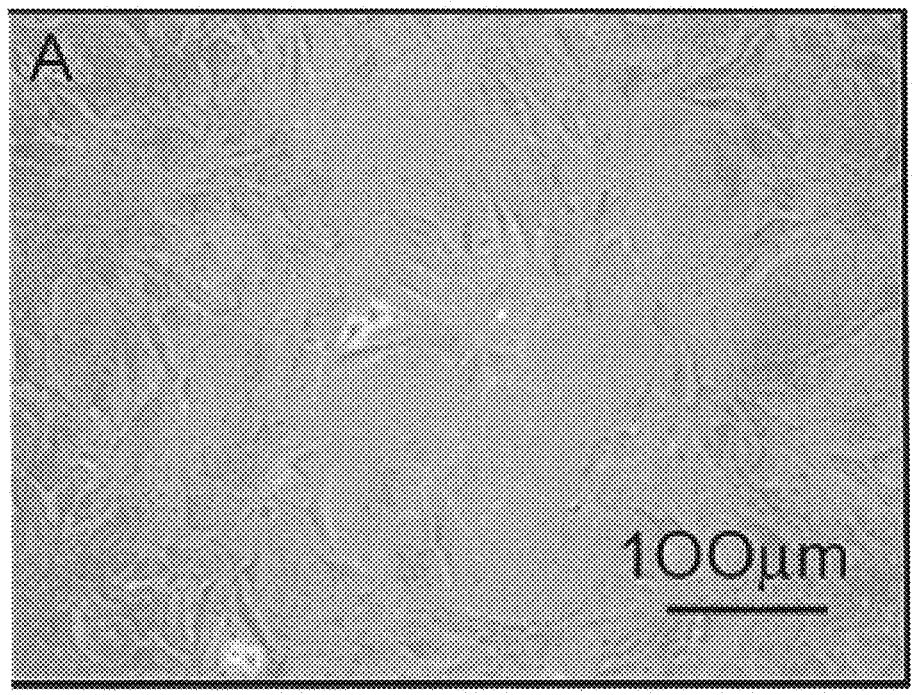
FIG. 3 shows a photomicrograph image of the morphology of aggrecan sensitive isolated dermis (DIAS) cells and normal fibroblasts grown on a tissue culture treated polystyrene after 7 Days of culture. (A) DIAS; (B) Fibroblasts.
Figure 3B:
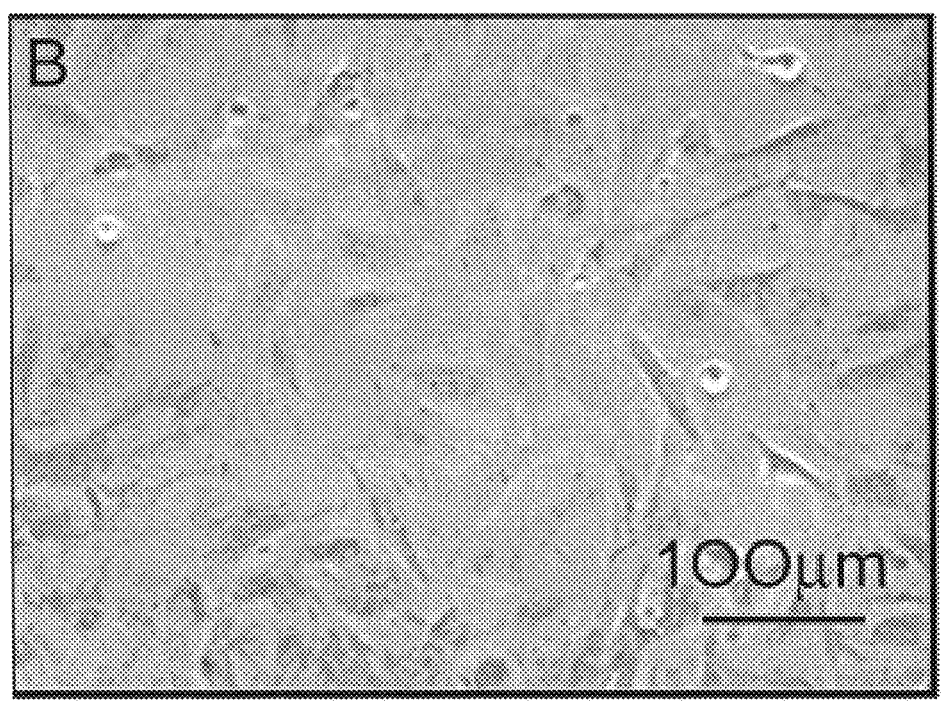

The morphological differences between fibroblasts and DIAS cells grown on aggrecan-coated surfaces was used to evaluate their abilities for chondrogenic differentiation. Almost all DIAS cells formed nodules, while no or very few nodules formed in fibroblast groups (See FIG. 5C, E). It seems that fibroblasts preferred the TCP surface rather than aggrecan-coated surface as evidenced by FIG. 3B and FIG. 5E, which implied the weak interaction between fibroblast and aggrecan. Certainly, some of the response to the chemical composition of the substrate is due to the surface topography, but surface chemistry plays a significant role as well. The influence of substrate on morphogenesis depends on cell type as well as cellular properties such as cytoskeletal organization, cell adhesion and the interaction of the cell with other cells. It has also been demonstrated herein that chondrocytes respond sensitively to aggrecan-coated surfaces by organizing themselves into nodules (FIG. 5A), suggesting a different interacting pathway against aggrecan-coated surface between chondrocytes and fibroblasts. Interestingly, DIAS cells employed an aggrecan-sensitive pathway significantly different from fibroblasts, but similar to that of chondrocytes by forming nodules with similar size and numbers on aggrecan-coated surfaces (FIG. 5A, C), suggesting similar cell-matrix interaction mechanisms may exist between DIAS cells and chondrocytes when cultured on an aggrecan substrate.

Detection of Cartilage Extracellular Matrix 24 well tissue culture treated plates were coated with aggrecan at a concentration of 10 μg/cm$^2$. Wells were rinsed with PBS prior to plating. Chondrocytes, DIAS cells and fibroblasts of passage 2 were plated at a concentration of $2 \times 10^5$ cells/well in 0.3 ml of medium. After 24 hrs, 0.7 ml medium was added in each well to reach a final volume of 1 ml. Triplicate samples from either control tissue culture plates or aggrecan-coated plates were collected at 24 hrs, 1 wk and 2 wk time points. Tissue culture treated 24 well plates were used as control.

To detect the presence of proteoglycans, at each time point, medium was carefully removed from the wells, and cells were washed with PBS. After a 10-min fixation in formalin, cells were rinsed with water and stained with Fast Green for 10 min. After a subsequent water wash, a brief incubation in acetic acid was performed. Immediately following the acid, Safranin O was added to the wells for 2 min. After a water rinse, cells were photographed using a Nikon CoolPix 990 digital camera mounted on a Nikon Eclipse TS-100 inverted microscope.

To detect the presence of collagen type II, wells were rinsed with PBS, fixed and pretreated with 0.3% hydrogen peroxide in PBS for 30 min at room temperature in order to block endogenous peroxidase activity. After washing with PBS three times, the cells were then treated with horse serum (Vectastain ABC kit) for 20 min to prevent non-specific binding. The cells were then incubated with the primary antibody (Chondrex, Redmond, Wash.) overnight at 4° C. The negative controls were incubated with PBS in place of primary antibody. After washing with PBS three times, the cells were then incubated with secondary biotinylated antirabbit goat IgG (Vectastain ABC kit) at room temperature for 30 min and then washed a further three times in PBS. Collagen type II was then visualized by using the streptavidin-biotin detection system (Vectastain ABC kit) and the substrate of diaminobenzidine tetrachloride (DAB) (Vector Laboratories, Burlingame, Calif.).

FIG. 6 shows the results of staining. Safranin-O staining performed on all tested groups found that all DIAS cells nodules formed in aggrecan-coated wells stained positive for proteoglycans, while DIAS cells on uncoated surfaces did not stain. Additionally, immunohistochemistry for type II collagen showed all nodules of cells cultured on aggrecan-coated surfaces stained positively, while DIAS cells on uncoated surfaces did not stain (FIG. 6, right). As seen by Safranin O staining and immunohistological staining, the cells synthesized chondrocyte-specific matrix in greater abundance than controls cells. This change in morphology and increase in matrix production suggest a chondrocytic phenotype. Furthermore, because these nodules are Safranin-O stain positive and type II collagen immunohistological stain positive, this suggests that DIAS cells undergo a chondrogenic process via a pathway related to aggrecan mediated signal transfer.

Detection of Gene Expression by Semi Quantitative RT-PCR Analysis of Cell Grown on Tissue Culture Treated Polystyrene With or Without Aggrecan.

RNA was isolated from the cultured cells using an Ambion RNAqueous kit from Ambion (Austin, Tex.). Briefly, provided lysis buffer was added to rinsed cells in the wells. The wells were scraped with the pipette tip to ensure complete lysis and cell collection. Samples were processed through the RNA isolation spin columns as described in the provided protocol. Elution was achieved in two steps using 30 μl of elution buffer. RNA was treated with DNase for 15 min at 65° C., followed by heating at 95° C. for 10 min. RNA was stored at −80° C. prior to use for reverse transcription reactions. For the reverse transcription reaction, 600 ng of RNA was incubated with buffer, 1 mM dNTPs, 1 mM random hexamers, RNase inhibitor and 100 U Stratagene StrataScript RT enzyme (La Jolla, Calif.) at 42° C. for 60 minute. After transcription was complete, samples were either stored at −20° C. or used immediately for PCR amplification using the Rotor-gene 3000 real-time PCR machine (Corbett Research, Sydney, AU). The real-time analysis used a 10 minute denaturing step, followed by 45 cycles of 30 seconds at 95° C., 30 seconds at 58° C., and 1 minute at 72° C., followed by a 2 minute extension. Fluorescence measurements were taken every cycle at 60° C. to provide a quantitative, real-time analysis of the genes analyzed. Primer sequences and concentrations are provided in Table 1 below.

TABLE 1

Primer sequences used for semi-quantitative real time PCR.

| Primer name | Forward Sequence (5' to 3')<br>Reverse Sequence (5' to 3')<br>Probe Sequence (5' to 3') | SEQUENCE ID. | Accession Number | Product Size |
|---|---|---|---|---|
| GAPDH | ACCCTCAAGATTGTCAGCAA | SEQ. ID NO. 1 | U85042 | 86 bp |
|  | ACGATGCCAAAGTGGTCA | SEQ. ID NO. 2 |  |  |
|  | CCTCCTGCACCACCAACTGCTT | SEQ. ID NO. 3 |  |  |

TABLE 1-continued

Primer sequences used for semi-quantitative real time PCR.

| Primer name | Forward Sequence (5' to 3')<br>Reverse Sequence (5' to 3')<br>Probe Sequence (5' to 3') | SEQUENCE ID. | Accession Number | Product Size |
|---|---|---|---|---|
| Type I collagen | CATTAGGGGTCACAATGGTC | SEQ. ID NO. 4 | NM_174520 | 97 bp |
|  | TGGAGTTCCATTTTCACCAG | SEQ. ID NO. 5 |  |  |
|  | ATGGATTTGAAGGGACAGCCTGGT | SEQ. ID NO. 6 |  |  |
| Type II collagen | AACGGTGGCTTCCACTTC | SEQ. ID NO. 7 | X02420 | 69 bp |
|  | GCAGGAAGGTCATCTGGA | SEQ. ID NO. 8 |  |  |
|  | ATGACAACCTGGCTCCCAACACC | SEQ. ID NO. 9 |  |  |
| Aggrecan | GCTACCCTGACCCTTCATC | SEQ. ID NO. 10 | U76615 | 76 bp |
|  | AAGCTTTCTGGGATGTCCAC | SEQ. ID NO. 11 |  |  |
|  | TGACGCCATCTGCTACACAGGTGA | SEQ. ID NO. 12 |  |  |

The effect of aggrecan on cartilage specific matrix gene expression was then investigated. DIAS cells and fibroblasts were grown on either aggrecan-coated tissue culture polystyrene or tissue culture treated polystyrene without aggrecan for 14 days. Steady-state levels of mRNA from each test group were collected for type II collagen and aggrecan measurement using quantitative real-time PCR. The aggrecan-coated surfaces strongly reduced aggrecan expression of DIAS cells from day 1 to day 7 compare to those of tissue culture treated control surface (FIG. 7) However, at 14 days the effect of aggrecan on aggrecan gene expression faded away. In contrast, no obvious differences could be observed between fibroblast groups with or without aggrecan (data not shown). Aggrecan treatment can inhibit aggrecan gene expression in DIAS cells.

Figure 8A:
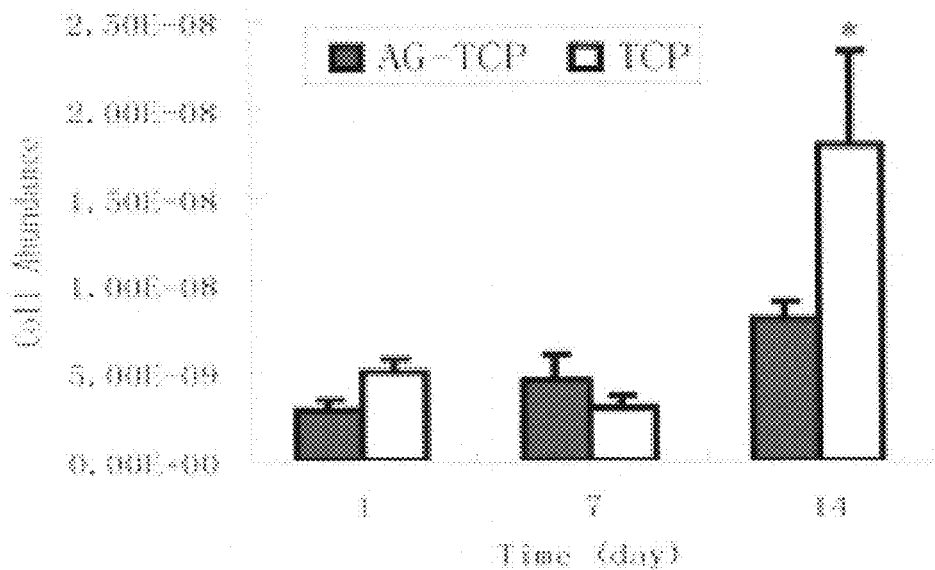
Figure 8B:
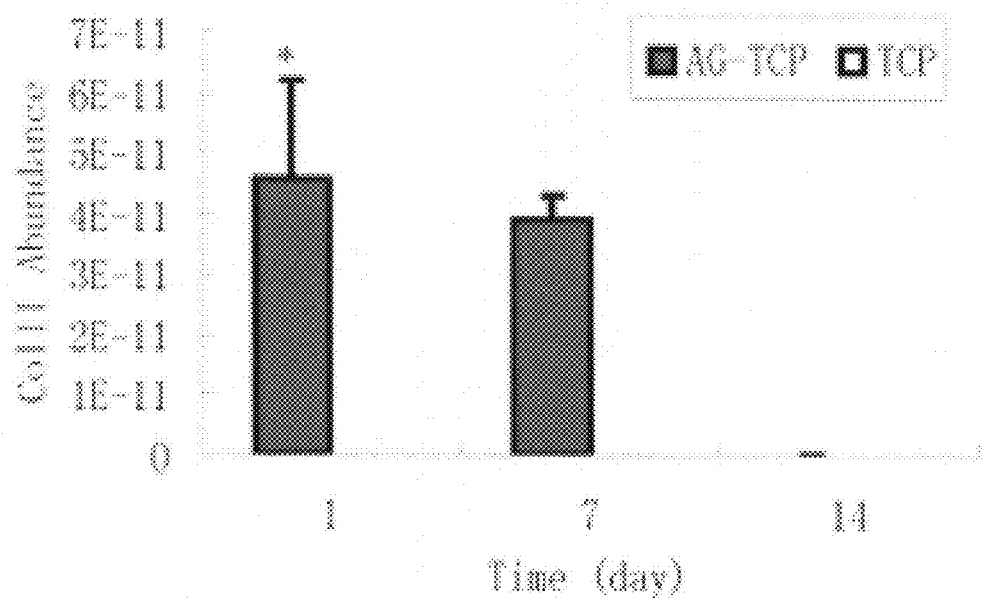
Figure 8C:
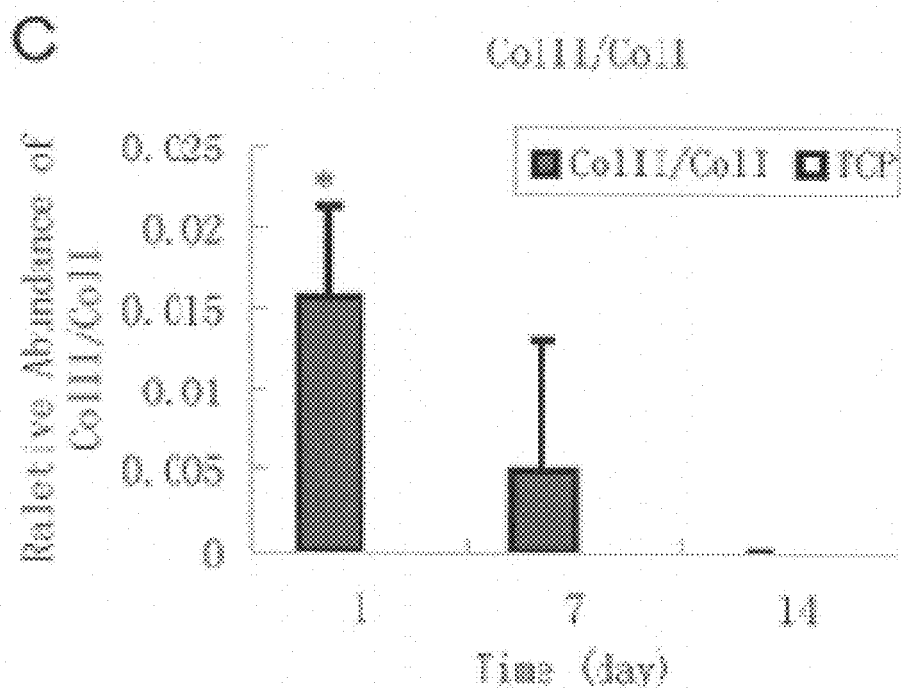

In addition, aggrecan treatment can inhibit collagen type I expression in DIAS cells (FIG. 8A). As messenger RNA is detectable at an earlier stage than the protein itself, expression of collagen type II message was determined by RT-PCR at each time point. Collagen type I expression was also determined to be correlated with fibroblastic characteristics. Initial results showed that collagen type II gene expression could only be detected in DIAS cells grown on the aggrecan-coated surfaces. An obvious inhibit of collagen type I gene expression was also observed at day 1 and day 7 in DIAS cells grown on aggrecan-coated surfaces. However the expression of collagens type II and I were highly time-dependent and the ratio of collagen type II to I (CII/CI), defined as an index of cell differentiation in chondrocytes, was significantly higher at the beginning of the culture (FIG. 8C). At the end of the experimental culture time, no collagen type II was detected in all tested groups (FIG. 8B). Parallel experiment showed that there are no differences between fibroblasts groups (data not shown).

FIG. 10 and FIG. 11 indicate the effect of aggrecan on aggrecan and collagen type I and II expression of DIAS cells cultured on tissue culture treated and non-tissue culture treated polystyrene coated with or without aggrecan. The results indicate that aggrecan-coated non-tissue culture surfaces are better for DIAS expression of collagen I and collagen II. The ratio of collagen I and collagen II indicate that non-tissue culture treated surfaces are better differentiated (FIG. 10). FIG. 11 indicates that aggrecan expression was suppressed in the presence of aggrecan coating. As a result, further investigation using non-tissue culture treated surfaces was performed. The results of the study of DIAS cells and fibroblasts cultured on non-tissue culture treated plates with or without aggrecan can be seen in FIGS. 15-18. Gene expression of collagen type I can be seen in FIG. 15 across all groups over a 14 day period of culture. Cartilage oligomeric protein gene expression can be seen in FIG. 16. FIGS. 17A and B show aggrecan abundance and gene expression over the 14 day culture period. FIG. 18 shows the collagen type II abundance in cell types over the 14 day culture period. These data suggest that the extent of chondroinduction undergone by DIAS cell cultures when cultured on aggrecan coated surfaces is higher than the degree of chondroinduction undergone by fibroblasts cultured under the same conditions.

Assessment of the Effect of Different Media on DIAS Cells and Fibroblasts Cultured on Non-Tissue Treated Polystyrene with or without Aggrecan.

24 well non-tissue culture treated plates were coated with aggrecan at a concentration of 10 µg/cm$^2$. Wells were rinsed with PBS prior to plating. DIAS cells and fibroblasts of passage 2 were plated at a concentration of $2 \times 10^5$ cells/well in 0.3 ml of medium (either culture medium or chondrogenic medium). After 24 hrs, 0.7 ml medium was added in each well to reach a final volume of 1 ml. Triplicate samples from either control non-tissue culture plates or aggrecan-coated plates were collected at 24 hrs, 1 wk and 2 wk time points. Non-tissue culture treated wells without aggrecan were used as control. Chondrogenic medium comprises Dulbecco's Modified Eagle Medium (DMEM) with 4.5 g/L-glucose and L-glutamine supplemented with $10^{-7}$ M dexamethasone, 50 µg/ml ascorbic acid, 40 µg/ml proline, 100 µg/ml sodium pyruvate, and 50 mg/ml ITS+Premix.

FIG. 12, FIG. 13, and FIG. 14 indicate the results of this study. Large quantities of Safranin-O stained positive nodules could be found in both aggrecan treated groups with normal medium and chondrogenic medium (FIG. 12). No nodule could be found in the groups grown on non aggrecan-coated surface with normal medium. The data imply that chondrogenic medium combined with non-tissue culture treated surfaces enhance nodule formation of DIAS cells at day 1. No nodules could be found in fibroblast group with normal medium from day 1 to day 14.

Furthermore, no nodules could be found in DIAS cells in normal medium after day 7, while large quantities of nodules could be found in chondrogenic medium groups. These nodules stain positive with Safranin-O for proteoglycans (FIG. 13) and stain positive for type II collagen (FIG. 14). Compared to previous experiments performed with tissue culture treated plates, aggrecan is required to get nodules on tissue culture treated surfaces, whereas with non-tissue culture treated surfaces, aggrecan is not needed but could obviously improve the formation of nodules. Non-tissue culture surfaces combined with chondrogenic medium could keep the nodules in culture for as long as 14 days.

Immunofluorescence of Cell Samples

Cell adhesion to the ECM plays a key role in the assembly of cells into functional multicellular organisms. To further our understanding of regulatory mechanisms between the testing groups in our study, P2 chondrocytes, DIAS cells and fibroblasts were cultured on aggrecan-coated surfaces for 36 hrs.

Cells for use in immunofluorescence experiments were grown directly on tissue culture treated plastic coverslips with and without aggrecan coating. After cultured for 36 hrs, they were rinsed with PBS, fixed in 4% paraformaldehyde, and permeabilized with a Triton-X solution. The cells were then blocked for 30 min in 1% BSA. For vinculin visualization, cells were incubated with monoclonal anti-vinculin IgG (1:300; Sigma), followed by Alexa 488-conjugated goat anti-mouse IgG (1:200, Molecular Probes, Eugene, Oreg.). F-actin was visualized by a 30 min exposure to rhodamine phalloidin (2 U/per coverslip; Molecular Probes, Eugene, Oreg.). After three final PBS washes, coverslips were then mounted between a microscope slide and glass coverslip using Pro-Long Gold with DAPI (Molecular Probes, Eugene, Oreg.). These samples were viewed with an Axioplan 2 microscope (Carl Zeiss, Oberkochen, Germany) and a CoolSNAP-HQ CCD camera (Photometrics, Tuscon, Ariz.). Images were acquired and analyzed using Metamorph 4.15 (Universal Imaging Corp., Downingtown, Pa.). After 36 hrs in culture, differences in the organization of F-actin and vinculin of chondrocytes, DIAS cells and fibroblasts grown on aggrecan-coated surfaces, as compared with cells grown on uncoated surfaces, were much more prominent.

Although all cells grown on aggrecan-coated surfaces exhibited high levels of F-actin and vinculin than cells grown on uncoated surfaces, obvious differences were seen among these aggrecan treated groups. Similar response patterns were observed in chondrocytes and DIAS cells to aggrecan stimuli, which is obviously different from those found in fibroblasts. For F-actin, chondrocytes and DIAS cells on aggrecan-coated surfaces showed patterns consisting of numerous, pronounced stress fibers running throughout the cell, parallel to each other or to the cell membrane of extended processes. By contrast, large numbers of fibroblasts developed poor stress fibers around a small volume of cytoplasm (FIGS. 9A, D and E). Similar vinculin-positive focal contacts pattern between chondrocytes and DIAS cells grown on aggrecan-coated surfaces were also shown, with restricted vinculin distribution to the cell periphery (FIG. 9A, C), while much lower vinculin-positive focal contacts were observed in fibroblasts grown on aggrecan-coated surfaces (FIG. 9E).

Similar shape, size, and cytoskeletal effects were observed between chondrocytes and DIAS cells (FIGS. 9A, C and a, c). Chondrocyte and DIAS cells grown on aggrecan-coated surfaces showed an increase in the presence of actin stress fibers and vinculin-containing focal adhesion points than cells grown on the uncoated TCP surfaces, and occupied larger surface area on the substratum. It is important to note that chondrocytes and DIAS cells are shown to perform similar f-actin and vinculin reorganization, which implied similar cell-ECM interaction and the consequent cellular events. Although the organization of f-actin in the current study was very similar to those reported for chondrocytes grown on monolayer, unlike chondrocytes grown in a monolayer, chondrocytes in situ contained no stress fibers, further work will be needed to illustrate the cytoskeleton reorganization under 3D culture condition. No significant differences were found in both fibroblast groups.

Analysis of the Morphology of Constructs.

After culture on aggrecan coated non-tissue culture treated surfaces for 14 days, DIAS cells, fibroblasts, and chondrocytes were transferred to hydrogel coated well surfaces and allowed to self-assemble.

The bottoms and sides of 96-well plates were coated with 100 µl 2% agarose (w/v), and the plates were shaken vigorously to remove excess agarose. The surface area at the bottom of the well in a 96-well plate is 0.2 cm$^2$. Chilled plates were then rinsed with culture medium before the introduction of cells.

Chondrogenically induced DIAS cells were then introduced into the hydrogel-coated wells at $4.8 \times 10^6$ cells per well in 300 µl of culture medium ($4.8 \times 10^6$ cells/0.2 cm$^2$ of hydrogel coated surface). The cells aggregated within 24 hrs, from which time 500 µl of the medium was changed every 2 days. After 2 weeks of culture, these cell aggregates were analyzed for extracellular matrix production. Fibroblasts and chondrocytes were used as control cells.

FIG. 20 is an image of developing constructs formed from fibroblasts and DIAS cells. DIAS cells self-assemble into cartilage-like constructs, outperforming fibroblast constructs; they also formed a much bigger construct than fibroblasts. FIG. 22 is an image of constructs formed by self-assembly of DIAS cells and fibroblasts cultured on aggrecan-coated non-TCP surfaces for 14 days. The results indicate that DIAS cells self-assemble better than the fibroblast group. Chondrocytes formed a much bigger construct than both DIAS cells and fibroblasts (not shown). Both DIAS and fibroblast constructs contracted, while no or light contraction was found in the chondrocyte group.

Detection of Cartilage Specific Extracellular Matrix in the Constructs

The constructs were stained using Safranin-O and immunohistochemical staining to detect the presence of proteoglycans and collagen, as described above. FIG. 21 indicates the results of staining. DIAS cell constructs produce less collagen type I than the fibroblast constructs. FIG. 23 indicates the results of staining of DIAS cell constructs, fibroblast constructs, and chondrocyte constructs. All cells were initially cultured on aggrecan-coated non-tissue culture treated surfaces for 14 days. Large quantities of proteoglycan and collagen type II were shown in chondrocyte and DIAS groups, while less cartilage specific extracellular matrix were shown in fibroblast group. Slight collagen type I was shown in fibroblast group, while no or less collagen type II was found in this group. Moreover, as illustrated in FIG. 19, oil red staining indicated differentiated DIAS cells.

Figure 4B:
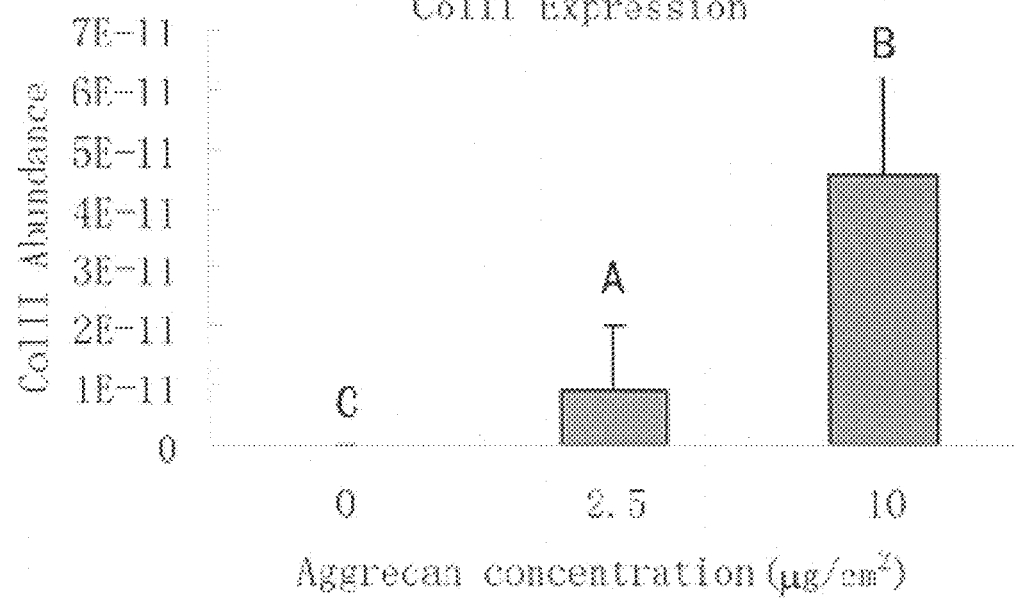
Figure 7:
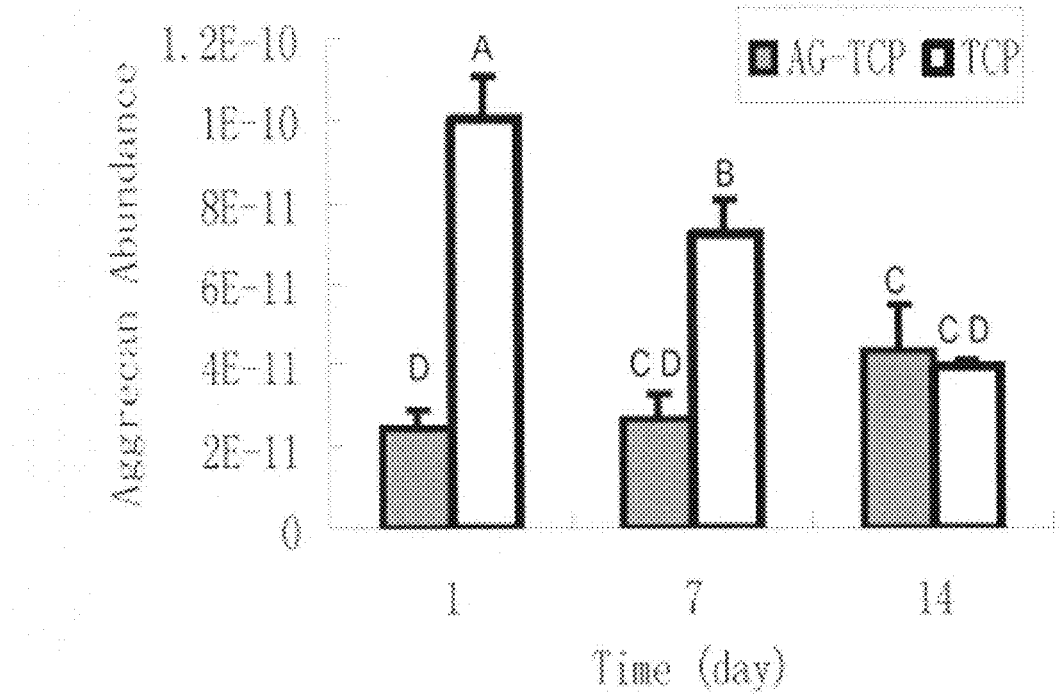
FIG. 7 is a graph of the effect of aggrecan coated surfaces on aggrecan expression of DIAS cells as a function of time in culture.

The present findings demonstrated that a specific subpopulation of fibroblastic cells could be isolated from goat skin dermis considering their fast adhering characteristic to TCP surfaces (FIG. 3), and these cells were demonstrated to have the potential of chondrogenic differentiation on aggrecan-coated surfaces by producing rich cartilage specific extracellular matrix (FIG. 6) and expressing cartilage specific gene (FIG. 7 and FIG. 8). The data presented herein also shows that DIAS cells rearranged their cytoskeleton organization by aggrecan-coated surfaces stimuli as chondrocytes did under same experimental condition (FIG. 8). Thus, the reorganization of f-actin and vinculin induced by the specific cell-matrix interaction may imply subsequent changes in various DIAS cells events, which may ultimately lead to chondrogenic phenotype formation of these cells (FIG. 4).

Chondroinduction of DIAS Cells in Monolayer Culture

Full-thickness abdomen skin specimens were obtained from 5 goats, separated from underlying adipose tissue, and digested with 0.5% Dispase at 4° C. overnight. The epidermis was then removed by scraping with a blade, and meticulously cleaned to remove all adipose tissue and blood coagulates in vessels. The dermis specimens were then washed, minced, and digested in phosphate buffered saline (PBS) containing 200 units/ml type II collagenase (Worthington, Lakewood, N.J.) at 37° C. for 15 hours with gentle rocking. After incubation, the cell suspensions were diluted at a ratio of 1:4 with expansion medium (Dulbecco's modified Eagle's medium [DMEM; Gibco, Grand Island, N.Y.] supplemented with 10% fetal bovine serum [FBS; BioWhittaker, Walkersville, Md.], 1% penicillin-streptomycin-amphotericin B [BioWhittaker], and 1% nonessential amino acids [Life Technologies, Gaithersburg, Md.]) and centrifuged at 300 g for 5 minutes. The cell pellets were resuspended in expansion medium and cultured in flasks. Cell yields were 5-12 million/cm$^2$ of skin. Medium was changed every 3-4 days. After confluence, cells were treated with 0.5% Dispase for 15 minutes, and the floating cells were discarded. After another 3 days of culture, cells from each animal were lifted using a solution containing 0.25% trypsin and 5 mM EDTA (Sigma, St. Louis, Mo.). These cells were combined and either plated to serve as the fibroblast control or purified to obtain DIAS cells.

To obtain the DIAS subpopulation, the lifted cells were seeded in a tissue culture-treated flask and allowed to attach for 10 minutes, after which the floating cells (F-DIAS) were removed. The attached cells, which represented <10% of the entire population, were washed 3 times with PBS and continued to be cultured in expansion medium for another 5 days. The cells were then harvested as DIAS cells for use in the subsequent chondroinduction process. For the monolayer portion of this study, day 0 was defined as the day that cells were to be seeded onto the aggrecan surface.

DIAS cells were chondroinduced by plating on aggrecan coated surfaces (ACS). The concentration of aggrecan (Sigma) was 10 µg/cm$^2$ per 24-well plate. DIAS cells, chondrocytes, and fibroblasts were seeded on ACS at a concentration of 2×10$^5$ cells/well in 0.3 ml of expansion medium. After 24 hours, 1 ml of chemically defined medium (DMEM containing 1% penicillin-streptomycin-amphotericin B, 1% nonessential amino acids, 10 ng/ml transforming growth factor β1 [PeproTech, Rocky Hill, N.J.], 100 ng/ml recombinant human insulin like growth factor [PeproTech], 10$^{-7}$M dexamethasone [Sigma], 50 µg/ml ascorbic acid-2-phosphate [Acros Organics, Geel, Belgium], 0.4 mM proline [Acros Organics], and 50 mg/ml ITS+Premix [BD Biosciences, Bedford, Mass.]) was changed in each well to reach a final volume of 1 ml, and the medium was changed every 2 days for 2 weeks. As positive controls, goat articular cartilage chondrocytes were obtained as previously described in Hu J C, Athanasiou K A. A self-assembling process in articular cartilage tissue engineering. Tissue Eng 2006; 12:969-79.

Chondroinduction Effects of Agggrecan on DIAS Cells in Monolayer Culture

Triplicate samples from each cell group were collected at 24 hours, 1 week, and 2 weeks and assessed for chondrocyte specific matrix using the following analyses. For chondrocytic nodule formation, samples were collected and photographed using a CoolPix 990 digital camera (Nikon, Melville, N.Y.) mounted on an Axioplan 2 microscope (Zeiss, Oberkochen, Germany).

For glycosaminoglycan (GAG) detection, Safranin O staining was performed after 10 minutes of formalin fixation. Cells were incubated with 1% acetic acid, and Safranin O was applied for 2 minutes. Cells were then photographed after a water rinse.

Type II collagen (CII) was detected using immunohistochemistry. Briefly, formalin fixed cells were incubated with CII primary antibody (Chondrex, Redmond, Wash.) and detected using the Vectastain ABC kit (Vector, Burlingame, Calif.) according to the instructions provided. A quantitative sandwich enzyme linked immunosorbent assay (ELISA) for CII was also performed, using a monoclonal capture antibody (6009) and a polyclonal detection antibody (7006) (Chondrex).

All nodules formed using DIAS cells on ACS stained positively for GAGs (FIG. 24A-C) and for CII (FIG. 24D-F). All cells grown on uncoated surfaces were negative for both stains. The formation of nodules exhibits GAGs and CII matrix provided evidence of chondroinduction of DIAS cells.

Quantification of Cartilage-Specific Matrix Gene Expression and Protein Production.

Semiquantitative reverse transcriptase-polymerase chain reaction (PCR) analyses were performed to measure the expression of type I collagen (CI), CII, cartilage oligomeric protein (COMP), and aggrecan. RNA isolated using an RNAqueous kit (Ambion, Austin, Tex.) was reverse-transcribed using StrataScript RT enzyme and kit (Stratagene, La Jolla, Calif.) at 600 ng RNA per reaction. After transcription, PCR was performed using the Rotor-Gene 3000 real-time PCR system (Corbett Life Science, Sydney, New South Wales, Australia). The real-time analysis consisted of 15 minutes at 95° C., followed by 55 cycles of 15 seconds at 95° C., and 30 seconds at 60° C. Primer and probe sequences and concentrations are shown in Table 1 above. The day 0 control was obtained by isolating messenger RNA (mRNA) from fibroblasts prior to seeding onto ACS.

The effect of ACS on cartilage-specific matrix gene expression and on protein production was investigated. DIAS cells and fibroblasts were grown either on ACS or on uncoated surfaces for 14 days. Expression of mRNA for 3 positive markers of chondroinduction (aggrecan, CII, and COMP) and 1 negative marker of chondroinduction (CI) was measured. In addition, ELISA was used to determine the actual protein synthesis level of CII.

After exposure to ACS, expression of CI immediately decreased in both DIAS cells and fibroblasts, although this suppression was initially more pronounced in DIAS cells. This suppression did not persist beyond 7 days (FIG. 25A).

By comparing the expression and synthesis of cartilage-specific markers, DIAS cells were shown to possess a greater chondroinduction potential compared with fibroblasts (FIG. 25). Specifically, after seeding onto ACS, aggrecan gene expression in DIAS cells was significantly higher (P<0.05) than that in fibroblasts at 7 and 14 days (FIG. 25B). Similarly, COMP expression by DIAS cells was also significantly higher (P<0.05) than that in fibroblasts (FIG. 25C) at 7 and 14 days. By day 14, COMP expression in DIAS cells was 5-fold higher than in fibroblasts. More important, protein synthesis levels of CII (FIG. 25D), another cartilage-specific marker, were found to mirror COL2 gene expression (data not shown) and were significantly higher (P<0.05) at all time points in DIAS cell populations when compared with fibroblasts (FIG. 25D).

Initiation of Chondroinduction by Fluorescence Imaging of Cytoskeletal Organization of ACS.

Immunofluorescence was used to detect filamentous actin (F-actin) and vinculin. After 36 hours of culture on ACS or uncoated control surfaces, cells were rinsed with PBS, fixed in 4% paraformaldehyde, permeabilized with Triton X-100, and blocked with 1% bovine serum albumin. For vinculin visualization, cells were incubated with monoclonal anti-vinculin IgG (Sigma), followed by incubation with Alexa Fluor 488-conjugated goat anti-mouse IgG (Molecular Probes, Eugene, Oreg.). F-actin was visualized using rhodamine and phalloidin staining (Molecular Probes). Slides were viewed using an Axioplan 2 microscope with a CoolSnapHQ CCD camera (Photometrics, Tucson, Ariz.).

Since cells adhere to the extracellular substratum by focal adhesion, we investigated whether ACS had any effect on this event. After 36 hours in culture, cells were labeled with phalloidin and rhodamine, which specifically bind to the F-actin cytoskeleton, and with anti-vinculin antibodies. Differences were observed among cell groups cultured on ACS (FIG. 26), but not among cells cultured on uncoated surfaces (results not shown). Fibroblasts seeded on ACS formed strong polarized F-actin fiber bundles distributed throughout the cytoplasm, accompanied by abundant stress fibers (FIG. 26C). In contrast, the formation of F-actin fiber bundles was significantly inhibited in both chondrocytes and DIAS cells (FIGS. 26A and B). In these cells, F-actin was preferentially lost from the central cytoplasm and became concentrated at the cell periphery. Treatment with antivinculin antibodies revealed that the distribution of vinculin in each cell mirrored F-actin distribution (FIGS. 26D and F).

Fabrication of In Vitro Cartilage-Like Constructs and Histologic Evaluation of Engineered Constructs.

Using the chondroinduction evaluation described above, 7 days was chosen as the optimal ACS exposure time for chondroinduction. Thus, chondrocytes, DIAS cells, or F-DIAS cells were plated on 24-well ACS at $2 \times 10^5$ cells/well. After 7 days, cells were harvested by scraping and were seeded to form self-assembled constructs, as previously described in Hu J C, Athanasiou K A. A self-assembling process in articular cartilage tissue engineering. Tissue Eng 2006; 12:969-79. Briefly, a silicon-positive die consisting of cylindrical prongs (3 mm diameter×10 mm long) was used to form a 2% agarose mold. The mold was then separated from the silicon-positive die and saturated with defined medium containing 1% FBS. For each construct, cells harvested from the 24 wells were combined and suspended in 50 µl of defined medium with 1% FBS and seeded into the agarose molds. Within 24 hours, the cells formed attached constructs, and these constructs were maintained in the agarose molds for 2 weeks. Medium was changed every 2 days. For the 3 D portion of this study, day 0 was defined as the day that cells were seeded into the agarose wells.

After 2 weeks, constructs were collected to evaluate cartilage-specific matrix deposition, using Safranin O to determine GAG distribution and immunohistochemistry to detect CII, CI, chondroitin 4-sulfate, and chondroitin 6-sulfate. Results are expressed as the mean±SD. Data were assessed by 3-factor analysis of variance. P values less than 0.05 were considered significant.

Cells in all groups aggregated and formed constructs in vitro, 2 weeks after self-assembly. Samples from each group were then collected and sectioned for histologic evaluation. Histologic and immunohistochemical studies in cartilage ECM from DIAS constructs revealed strong and even staining for GAGs, CII, chondroitin 4 sulfate, and chondroitin 6-sulfate (FIGS. 27B, E, H, and K). In contrast, the F-DIAS groups stained poorly for all the above-mentioned cartilage components (FIGS. 27C, F, I, L, and 0). CI was not observed in either the chondrocyte or the DIAS constructs, while colonies of cells positive for CI (FIG. 27O, arrows) were detected in F-DIAS groups. This, in combination with the observation that a trace amount of CII was localized in colonies within F-DIAS cells (FIG. 27F, arrows), implies that complex heterogeneous cell populations exist within the F-DIAS constructs in terms of their chondroinduction potential.

As illustrated above, a modified rapid adherence process was developed to isolate DIAS cells from goat dermis for chondroinduction. Instead of selecting all rapidly adhering cells from the dermis, the Dispase-sensitive subpopulations are first removed (since these populations also contain rapidly adhering cells). Rapidly adhering cells from the remaining sub populations are then isolated based on their adherence time. Cells that adhered to the plastic surface within 10 minutes were chosen because they produced the highest nodule numbers when seeded on ACS compared with cells from other time points (data not shown).

The preceding examples illustrate that DIAS cells were chondroinduced when seeded on ACS, and were phenotypically, morphologically, and functionally similar to chondrocytes. In situ activity of DIAS cells might be suppressed in the in vivo microenvironment through signaling from skin ECM and/or from mature fibroblasts. However, in vitro or ectopically, the chondroinduction process may be initiated due to the presence of an enriched environment of DIAS cells and/or exposure to aggrecan or other cartilage-specific ECM components.

Chondrocytes, DIAS cells, and fibroblasts were seeded on ACS in this study. Fibroblasts showed a spindle-like morphology on ACS 24 hours after seeding. However, we found that chondrocytes responded sensitively to ACS by organizing into nodules, suggesting the presence of a different interacting pathway between chondrocytes and fibroblasts. DIAS cells used an aggrecan-sensitive pathway significantly different from that of fibroblasts. However, DIAS cells formed nodules similar in size and number to those in chondrocytes on ACS, suggesting that analogous early-stage cell-matrix interaction mechanisms may exist between DIAS cells and chondrocytes when cultured on ACS.

Consistent with the morphologic findings, the ECM results also show that DIAS cells have a higher potential for chondroinduction compared with unpurified, heterogeneous fibroblast subpopulations. Throughout the entire experimental period, nodules formed by DIAS cells seeded on ACS were shown to stain positively for Safranin O and for CII. In contrast, both DIAS and fibroblast cells seeded on uncoated surfaces showed negative staining for both GAG and CII under the same conditions, which is common for dermis-derived cells. DIAS cells exposed to ACS expressed cartilage marker genes more rapidly and more potently than did fibroblasts. Moreover, ACS appeared to inhibit the fibroblastic phenotype in DIAS cells, as evidenced by significant inhibition of collagen type I gene expression at 1 day and 7 days.

However, it was also observed that collagen type I gene expression recovered with time in each cell group, and, since higher levels of expression of other cartilage specific markers were seen from 7 days onward, 7 days was chosen as the transition between monolayer and 3-D culture. Compared with 3-D culture, 2-dimensional (2-D) surfaces appeared less optimal for chondroinduction. This was confirmed by immunohistochemistry of 3-D cultures. Indeed, CI was not observed in self-assembled DIAS constructs, while cartilage-specific markers were retained (FIGS. 27B, E, H, and K).

Taken together, these findings confirmed that DIAS cells have higher chondroinduction potential than fibroblasts when exposed to ACS.

The influence of substrate on morphogenesis depends on cell type as well as cellular properties such as cytoskeletal organization, cell adhesion, and cell-cell interactions. To further an understanding of the regulatory mechanisms of aggrecan, chondrocytes, DIAS cells, and fibroblasts were cultured on ACS for 36 hours. Chondrocytes and DIAS cells were found to organize their F-actin on ACS in a similar pattern, which was significantly different from that of fibroblasts. Fewer stress fibers were found in DIAS cells and chondrocytes than in fibroblasts. Furthermore, the distribution of vinculin in each group mirrored its F-actin distribution (FIG. 26). The observed F-actin patterns of DIAS cells and chondrocytes in this study were similar to those reported for chondrocytes in monolayer. This implies that the 2 cell types have similar cell-matrix interactions.

Studies of a number of cell types have shown that F-actin organization plays an important role in a large number of cellular events, including shape alteration, cell signaling, secretion, and ECM assembly. Any one or a combination of the above described events may thus be precipitated by the F-actin organization brought about by cell matrix interactions. Indeed, chondrocytes were found to respond to ECM components, including hyaluronic acid) and CI), by reorganizing their F-actin in vitro, resulting in the regulation of various chondrocyte behaviors such as cell shape determination, chondrogenesis initiation, chondrocytic phenotype maintenance, and chondrocyte hypertrophy. Again, any one or a combination of these events may have occurred as chondrocytes were seeded onto ACS. In this study, specific cell-matrix interactions led to F-actin and vinculin reorganization. This reorganization may have resulted in the subsequent changes in various DIAS cell events that ultimately led to chondrogenic phenotype formation of these cells in 2-D. These specific cell matrix interactions may also lead to a temporal and spatial self-assembly process in 3-D.

The assembly of cells into functional multicellular organisms in 3 dimensions involves F-actins, the primary sites at which cells detect and adhere to their ECM. Points of F-actin and vinculin colocalization have been shown to be sites where chondrocytes adhere to the articular cartilage ECM. For these purposes, a self-assembly process has recently been developed. By using this scaffoldless approach with chondrocytes, cartilage-like constructs have successfully been obtained that mimic native cartilage in terms of biochemical and biomechanical properties. Although the exact mechanisms of the self-assembly process initiated and accomplished by chondrocytes are not known, temporal and spatial interactions between the chondrocytes and their ECM environments have been suggested to be essential for successful cartilage development.

When chondroinduced DIAS cells were seeded in agarose molds, they aggregated and self-assembled into cartilage-like constructs, as expected. Two weeks after seeding, the constructs were sectioned for cartilage-specific ECM detection. Similar to constructs formed by chondrocytes, high levels of total GAG, CII, chondroitin 4-sulfate, and chondroitin 6-sulfate were found in DIAS constructs (FIGS. 27A, B, D, E, G, H, J, and K), which indicated cartilage formation. In contrast, F-DIAS cell constructs showed poor staining for all of the above mentioned cartilage-specific matrices; instead, colonies of cells that stained positively for CI were detected. Furthermore, compared with the homogeneous distribution of cartilage specific ECM in DIAS constructs, colonies of cells that stained positively for CI (FIG. 27O, arrows) and CII (FIG. 27F, arrows) showed an uneven distribution of different dermis derived sub populations in the F-DIAS constructs. This further supports the hypothesis that subpopulations of dermis derived cells must first be purified, in order to obtain cells that can undergo chondroinduction in a uniform manner.

Differences in ECM levels between chondrocyte constructs and DIAS constructs still exist. This may be remedied by optimizing the protocol to use different adhesion times to select for DIAS cells with higher chondroinduction potential. In addition to ACS, optimized combinations of growth factors might be important in chondroinduction and the subsequent self-assembly of the DIAS cells.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method for inducing differentiation of cells into chondrocytes comprising providing a plurality of dermis-isolated, aggrecan sensitive (DIAS) cells and placing the plurality of DIAS cells in contact with an aggrecan coated surface, wherein the plurality of DIAS cells maintain rounded morphology when placed in contact with the aggrecan coated surface.

2. The method of claim 1 further comprising:
isolating the plurality of DIAS cells from skin using enzymatic digestion; and
purifying the plurality of DIAS cells by allowing the DIAS cells to attach to a tissue-culture treated surface within a defined period of time and removing those cells which do not attach to the surface within the defined period of time.

3. The method of claim 1 further comprising:
isolating the plurality of DIAS cells from skin using enzymatic digestion; and
purifying the plurality of DIAS cells using density gradient separation.

4. The method of claim 1 wherein the aggrecan coated surface is coated with aggrecan at a concentration of from about 0.1 to about 100 µg/cm².

5. The method of claim 1 wherein the aggrecan coated surface is coated with aggrecan at a concentration of from about 1 to about 50 µg/cm².

6. The method of claim 1 wherein the aggrecan coated surface comprises one or more of keratin sulfate, chondroitin sulfate, and hyaluronate.

7. A method comprising:
providing a plurality of chondrogenically induced DIAS cells, wherein the plurality of chondrogenically induced DIAS cells associate into a plurality of nodules on an aggrecan coated surface;
seeding the plurality of chondrogenically induced DIAS cells onto a hydrogel coated culture vessel; and
allowing the plurality of chondrogenically induced DIAS cells to self-assemble into a tissue engineered construct.

8. The method of claim 7 wherein the hydrogel coated culture vessel is coated with aggrecan at a concentration of from about 0.1 to about 100 µg/cm².

9. The method of claim 7 wherein the hydrogel coated culture vessel comprises hydrogel comprising one or more of agarose, alginate, and polyHEMA.

10. The method of claim 7 further comprising molding the tissue engineered construct into a desired shape.

11. The method of claim 7 further comprising molding the tissue engineered construct into a desired shape, wherein molding comprises transferring the tissue engineered construct to a shaped hydrogel negative mold, applying a shaped hydrogel positive mold to the negative mold to form a mold-construct assembly, and culturing the mold-construct assembly.

12. The method of claim 7 further comprising molding the tissue engineered construct into a desired shape, wherein the desired shape is in the shape of at least a portion of a joint, cartilaginous tissue of a mammal, tendon tissue of a mammal, or ligament tissue of a mammal.

13. The method of claim 7 further comprising molding the tissue engineered construct into a desired shape, wherein the desired shape is in the shape of at least a portion of a femur or a temporomandibular joint.

14. The method of claim 7 further comprising exposing the plurality of chondrogenically induced DIAS cells, the tissue engineered construct or both to a pressure, a load or both.

15. The method of claim 7 wherein the cells or constructs or both are treated with staurosporine or a Rho-associated kinase (ROCK) inhibitor or both.

16. The method of claim 7 wherein the plurality of chondrogenically induced DIAS cells, the tissue engineered construct or both are treated with one or more growth factors.

17. The method of claim 7 wherein the plurality of chondrogenically induced DIAS cells, the tissue engineered construct or both are treated with one or more growth factors chosen from TGF-beta 1, TGF-beta 3, BMP-2, BMP-4, and IGF-I.

18. The method of claim 7 further comprising implanting the tissue engineered construct in a subject.

* * * * *